(12) United States Patent
Daniell

(10) Patent No.: US 9,605,045 B2
(45) Date of Patent: Mar. 28, 2017

(54) EXPRESSION OF THE HUMAN IGF-1 IN TRANSGENIC PLASTIDS

(71) Applicant: The Trustees of the University of Pennsylvania, Philadelphia, PA (US)

(72) Inventor: Henry Daniell, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/553,647

(22) Filed: Nov. 25, 2014

(65) Prior Publication Data

US 2015/0096082 A1   Apr. 2, 2015

Related U.S. Application Data

(63) Continuation of application No. 10/519,820, filed as application No. PCT/US03/21159 on Jul. 3, 2003, now abandoned.

(60) Provisional application No. 60/393,439, filed on Jul. 3, 2002.

(51) Int. Cl.
*C12N 15/82* (2006.01)
*C07K 14/65* (2006.01)
*A61K 38/00* (2006.01)

(52) U.S. Cl.
CPC .......... *C07K 14/65* (2013.01); *C12N 15/8214* (2013.01); *C12N 15/8257* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,629,175 A * | 5/1997 | Goodman | C07K 14/57 435/69.1 |
| 5,633,153 A | 5/1997 | Ursin | |
| 5,693,507 A | 12/1997 | Daniell | |
| 5,776,897 A * | 7/1998 | Lewis | C07K 14/65 514/17.7 |
| 5,866,421 A * | 2/1999 | McBride | C07K 14/325 435/320.1 |
| 5,877,402 A | 3/1999 | Maliga et al. | |
| 5,932,479 A | 8/1999 | Daniell | |
| 7,795,497 B2 * | 9/2010 | Daniell | C12N 9/0008 800/278 |

FOREIGN PATENT DOCUMENTS

| | | | |
|---|---|---|---|
| WO | 9910513 | | 3/1999 |
| WO | WO 99/10513 | * | 4/1999 |
| WO | WO/99/10513 | | 4/1999 |
| WO | WO 00/03022 | * | 1/2000 |
| WO | WO/00/03022 | | 1/2000 |
| WO | 0164850 | | 9/2001 |
| WO | 0164927 | | 9/2001 |
| WO | 0164929 | | 9/2001 |
| WO | 0172959 | | 10/2001 |

OTHER PUBLICATIONS

Rall et al., Human insulin-like growth factor I and II messenger RNA: Isolation of complementary DNA and analysis of expression, Methods Enzymol., 1987, 239-248, 146.
Daniell et al., Multigene engineering: dawn of an exciting new era in biotechnology, Curr Opin Biotechnol., 2002, 136-41, 13(2).
Daniell et al., Milestones in chloroplast genetic engineering: an environmentally friendly era in biotechnology, Trends Plant Sci., 2002, 84-91, 7(2).

* cited by examiner

*Primary Examiner* — Anne Kubelik
(74) *Attorney, Agent, or Firm* — Kathleen D. Rigaut

(57) ABSTRACT

A plastid transformation vector for stably transforming a plastid genome, comprising, as operably-linked components, a first flanking sequence, a DNA sequence coding for synthetic insulin-like growth factor-1 (IGF-1s) (SEQ ID NO. 1) or a substantially homologous DNA sequence of IGF-1s, which is capable of expression in the plastid genome, and a second flanking sequence.

9 Claims, 8 Drawing Sheets

Native IGF-1 ggaccggagacgctctgcggggctgagctggtggatgctcttcagttcgtgtgtggagacaggggcttttatttcaacaagcccacagg
gtatggctccagcagtcggagggcgcctcagacaggcatcgtggatgagtgctgcttccggagctgtgatctaaggaggctggagatg
tattgcgcaccctcaagcctgccaagtcagct

Figure 1A

Synthetic IGF-1 ggtcctgaaactttatgtggtgctgaattagtagatgctttacaattcgtatgtggtgatcgtggtttctatttcaacaaacctactggttacggt
tcttcttctcgtcgtgctcctcaaactggtattgtagatgaatgttgttccgttcttgtgatttacgtcgtttagaaatgtactgtgctcctttaaaa
cctgctaaatctgct

Figure 1B

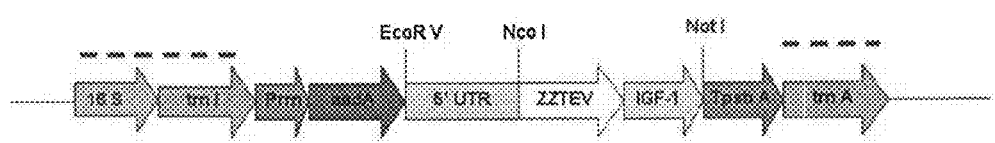
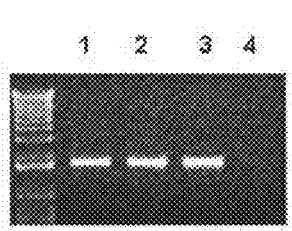
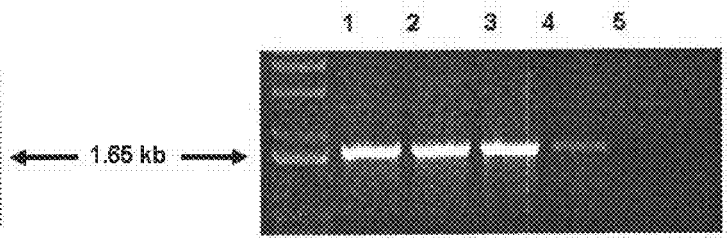
Figure 3A
Figure 3B ←— 1.65 kb —→ Figure 3C
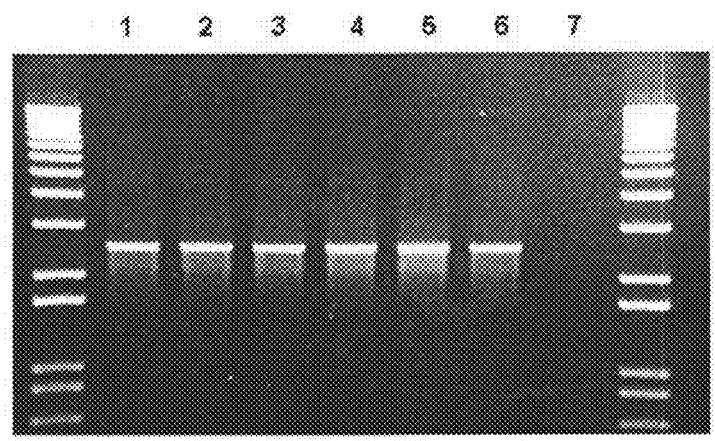
Figure 3D

EXPRESSION OF THE HUMAN IGF-1 IN TRANSGENIC PLASTIDS

The present application is continuation application of U.S. patent application Ser. No. 10/519,820 filed Dec. 30, 2004, which is a §371 application of PCT/US03/21159 filed Jul. 3, 2003 which in turn claims priority to U.S. Provisional Application No. 60/393,439, filed Jul. 3, 2002, the entire disclosure of each being incorporated by reference as though set forth in full.

FIELD OF THE INVENTION

This application relates to the field of genetic engineering of plant plastid genomes, particularly chloroplast, vectors for transforming plastids, transformed plants, progeny of transformed plants, and to methods for transforming plastid genomes of plants to generate Human insulin Growth factor (IGF).

BACKGROUND

Insulin-like growth factor 1 (IGF-1) is an anabolic hormone produced in the liver that is stimulated by the growth hormone (GH). GH binds to the GH receptors on the hepatocyte cell membrane and triggers an unknown mechanism that synthesizes and releases IGF-1 into the blood. The normal levels of IGF-1 are between 120-400 ng/ml. IGF-1 is involved in the regulation of cell proliferation and differentiation of a wide variety of cell and tissue types, and plays an important role in tissue renewal and repair. Because of these important applications of IGF-1 in the body, people who suffer IGF-1 deficiency have many harmful side effects. For example of this is patients with liver cirrhosis who have a reduction of the GH receptor in the hepatocytes and the diminished synthesis of the liver parenchyma causes a significant decrease of IGF-I levels in the blood (20 ng/ml and frequently to undetectable levels) with different systemic problems like muscle atrophy, osteopenia, hypogonadism, protein-calorie malnutrition, weight loss, and many others. Recent studies showed that treatments with low doses of IGF-I help to induce significant improvements in nutritional status, intestinal absorption, hypogonadism, and liver functions in rats with liver cirrhosis. Replacement therapy with IGF-1 in liver cirrhosis patients requires daily doses of 1.5 to 2 mg. Thus, a single patient would need to consume about 600 mg/year. However, the IGF-1 treatment is very expensive, $30,000/mg. Besides, as described above, IGF-1 is used in treatment of dwarfism, diabetes, osteoporosis, starvation, and hypercatabolism.

The insulin-like growth factors I and II (IGF-I and IGF-II, respectively) mediate multiple effects in vivo, including cell proliferation, cell differentiation, inhibition of cell death, and insulin-like activity (reviewed in Clark and Robinson, Cytokine Growth Factor Rev., 7: 65-80 (1996); Jones and Clemmons, Endocr. Rev., 16: 3-34 (1995)). Most of these mitogenic and metabolic responses are initiated by activation of the IGF-I receptor, an .alpha..sub.2.beta..sub.2-heterotetramer closely related to the insulin receptor (McInnes and Sykes, Biopoly., 43; 339-366 (1997); Ullrich et al., EMBO J., 5: 2503-2512 (1986)). Both proteins are members of the tyrosine kinase receptor superfamily and share common intracellular signaling cascades (Jones and Clemmons, supra). IGF-insulin hybrid receptors have been isolated, but their function is unknown. The IGF-I and insulin receptors bind their specific ligands with nanomolar affinity. IGF-I and insulin can cross-react with their respective non-cognate receptors, albeit at a 100-1000-fold lower affinity (Jones and Clemmons, supra). The crystal structure describing part of the extracellular portion of the TGF-I receptor has recently been reported (Garrett et al., Nature, 394: 395-399 (1998)). When referring to IGF-1 in this application it should be understood that the aspects of this invention may utilize all IGF-1 and all variants of IGF-1 which have been described in the art.

IGF-I is a single-chain 70-amino-acid protein with high homology to proinsulin. Unlike the other members of the insulin superfamily, the C region of the IGF's is not proteolytically removed after translation. The solution NMR structures of IGF-I (Cooke et al., Biochemistry, 30: 5484-5491 (1991); Hua et al., J. Mol. Biol., 10 259: 297-313 (1996)), mini-IGF-I (an engineered variant lacking the C-chain; DeWolf et al., Protein Science, 5: 2193-2202 (1996)), and IGF-II (Terasawa et al., EMBO J., 13: 5590-5597 (1994); Torres et al., J. Mol. Biol. 248: 385-401 (1995)) have been reported. It is generally accepted that distinct epitopes on IGF-I are used to bind receptor and binding proteins. It has been demonstrated in animal models that receptor-inactive IGF mutants are able to displace endogenous IGF-I from binding proteins and hereby generate a net IGF-I effect in vivo (Loddick et al., Proc. Natl. Acad. Sci. USA, 95: 1894-1898 (1998); Lowman et al., Biochemistry, 37: 8870-8878 (1998)). While residues Y24, Y29, Y31, and Y60 are implicated in receptor binding, IGF mutants thereof still bind to IGFBPs (Bayne et al., J. Biol. Chem., 265: 15648-15652 (1990); Bayne et al., J. Biol. Chem., 264: 11004-11008 (1989); Cascieri et al., Biochemistry, 27: 3229-3233 (1988); Lowman et al., supra.

Other IGF-I variants have been disclosed. For example, in the patent literature, WO 96/33216 describes a truncated variant having residues 1-69 of authentic IGF-I. EP 742,228 discloses two-chain IGF-I superagonists which are derivatives of the naturally occurring single-chain IGF-I having an abbreviated C domain. The IGF-I analogs are of the formula: BC$^n$A wherein B is the B domain of IGF-I or a functional analog thereof, C is the C domain of IGF-I or a functional analog thereof, n is the number of amino acids in the C domain and is from about 6 to about 12, and A is the A domain of IGF-I or a functional analog thereof.

Additionally, Cascieri et al., Biochemistry, 27: 3229-3233 (1988) discloses four mutants of IGF-I, three of which have reduced affinity to the Type 1 IGF receptor. These mutants are: (Phe$^{23}$, Phe$^{24}$, Tyr$^{25}$) IGF-I (which is equipotent to human IGF-I in its affinity to the Types 1 and 2 IGF and insulin receptors), (Leu$^{24}$) IGF-I and (Ser$^{24}$) IGF-I (which have a lower affinity than IGF-I to the human placental Type 1 IGF receptor, the placental insulin receptor, and the Type 1 IGF receptor of rat and mouse cells), and desoctapeptide (Leu$^{24}$) IGF-I (in which the loss of aromaticity at position 24 is combined with the deletion of the carboxyl-terminal D region of hIGF-I, which has lower affinity than (Leu$^{24}$) IGF-I for the Type 1 receptor and higher affinity for the insulin receptor). These four mutants have normal affinities for human serum binding proteins.

Bayne et al., J. Biol. Chem., 264: 11004-11008 (1988) discloses three structural analogs of IGF-I: (1-62) IGF-I, which lacks the carboxyl-terminal 8-amino-acid D region of IGF-I; (1-27, Gly$^4$, 38-70) IGF-I, in which residues 28-37 of the C region of IGF-I are replaced by a four-residue glycine bridge; and (1-27, Gly$^4$, 38-62) IGF-I, with a C region glycine replacement and a D region deletion. Peterkofsky et al., Endocrinology, 128: 1769-1779 (1991) discloses data using the Gly$^4$ mutant of Bayne et al., supra, Vol. 264. U.S. Pat. No. 5,714,460 refers to using IGF-I or a compound that increases the active concentration of IGF-I to treat neural damage.

Cascieri et al., J. Biol. Chem., 264: 2199-2202 (1989) discloses three IGF-I analogs in which specific residues in the A region of IGF-I are replaced with the corresponding residues in the A chain of insulin. The analogs are: (Ile.sup.41, Glu.sup.45, Gln. sup.46, Thr.sup.49, Ser.sup.50, Ile.sup.51, Ser. sup.53, Tyr.sup.55, Gln.sup.56) IGF-I, an A chain mutant in which residue 41 is changed from threonine to isoleucine and residues 42-56 of the A region are replaced; (Thr.sup.49, Ser.sup.50, Ile.sup.51) IGF-I; and (Tyr.sup.55, Gln.sup.56) IGF-I.

WO 94/04569 discloses a specific binding molecule, other than a natural IGFBP, that is capable of binding to IGF-I and can enhance the biological activity of IGF-I. WO 98/45427 published Oct. 15, 1998 and Laowman et al., supra, disclose IGF-I agonists identified by phage display. Also, WO 97/39032 discloses ligand inhibitors of IGFBP's and methods for their use.

There are various forms of human insulin on the market that differ in the duration of action and onset of action, but have the native human sequence. Jens Brange, Galenics of Insulin, The Physico-chemical and Pharmaceutical Aspects of Insulin and Insulin Preparations (Springer-Verlag, N.Y., 1987), page 17-40. Regular insulin is a clear neutral solution that contains hexameric insulin. It is short acting, its onset of action occurs in 0.5 hour after injection and duration of action is about 6-8 hours. NPH (Neutral Protamine Hagedorn) insulin, also called Isophane Insulin, is a crystal suspension of insulin-protamine complex. These crystals contain approximately 0.9 molecules of protamine and two zinc atoms per insulin hexamer. Dodd et al., Pharmaceutical Research, 12: 60-68 (1995). NPH-insulin is an intermediate-acting insulin; its onset of action occurs in 1.5 hours and its duration of action is 18-26 hours. 70/30 insulin is composed of 70% NPH-insulin and 30% Regular insulin There are also Semilente insulin (amorphous precipitate of zinc insulin complex), UltraLente insulin (zinc insulin crystal suspension), and Lente insulin (a 3:7 mixture of amorphous and crystalline insulin particles). Of the various types of insulins available, NPH-, 70/30, and Regular insulin are the most widely used insulins, accounting for 36%, 28%, and 15%. respectively, of the insulin prescriptions in 1996.

The use of recombinant DNA technology and peptide chemistry have allowed the generation of insulin analogs with a wide variety of amino acid substitutions, and IGF-like modifications to insulin have been made for the purpose of modifying insulin pharmacokinetics (Brange et al., Nature, 333: 679 (1988); Kang et al., Diabetes Care, 14: 571 (1991); DiMarchi et al., "Synthesis of a fast-acting insulin analog based upon structural homology with insulin-like growth factor-I," in: Peptides: Chemistry and Biology, Proceedings of the Twelfth American Peptide Symposium, J. A. Smith and J. E. Rivier, eds. (ESCOM, Leiden, 1992), pp. 26-28; Weiss et al., Biochemistry, 30: 7373 (1991); Howey et al., Diabetes, 40: (Supp 1) 423A (1991); Slieker and Sundell, Diabetes, 40: (Supp 1) 168A (1991); Cara et al., J. Biol. Chem., 265: 17820 (1990); Wolpert et al., Diabetes, 39: (Supp 1) 140A (1990); Bornfeldt et al., Diabetologia, 34: 307 (1991); Drejer, Diabetes/Metabolism Reviews, 8: 259 (1992); Slieker et al., Adv. Experimental Med. Biol., 343; 25-32 (1994)). One example of such an insulin analog is Humalog.™ insulin (rapid-acting monomeric insulin solution, as a result of reversing the Lys (B28) and Pro (B29) amino acids on the insulin B-chain) that was recently introduced into the market by Eli Lilly and Company. A review of the recent insulin mutants in clinical trials and on the market is found in Barnett and Owens, Lancet, 349: 47-51 (1997).

Additionally, a variant designated (1-27, gly.sup.4, 38-70) hIGF-I, wherein residues 28-37 of the C region human IGF-I are replaced by a four-residue glycine bridge, has been discovered that binds to IGFBP's but not to IGF receptors (Bar et al., Endocrinology, 127: 3243-3245 (1990)).

Currently, most of the IGF-1 that is available is expressed in E. coli. The main problem with this expression system is that E. coli cannot produce the mature IGF-1 because E. coli does not form disulfide bonds in the cytoplasm. The polypeptide has to be targeted in the periplasm to form disulfide bonds. The cost of IGF-1 production increases when the protein is in the periplasm because it is harder to purify and the IGF-1 is not properly folded because the disulfide bonds were not formed. Transgenic plants are good expression systems for large-scale production of recombinant proteins at industrial levels. Plant systems have many advantages, such as: the low cost of growing plants on a large scale, the availability of natural protein storage organs, and the established practices for their efficient harvesting, transporting, storing, and processing. It has been estimated that the cost of producing recombinant proteins in plants could be 10 to 50 fold lower than producing the same protein by E. coli via fermentation. A drawback of the plant systems is the low expression levels of recombinant proteins. In general, proteins produced in nuclear transgenic plants are relatively low, mostly less than 1% of the total soluble protein. Some examples of these proteins are human serum albumin 0.02%, hemoglobin 0.05%, and erythropoietin 0.0026% of total soluble protein. Also, a synthetic gene coding for the human epidermal growth factor was expressed only up to 0.001% of total soluble protein in transgenic tobacco. One of the reasons for low expression levels is that in nuclear transformation the gene is inserted randomly resulting in position effect or the expression of transgene is silenced. To avoid these problems the proteins can be expressed in the plastid. Chloroplast transformation is a recent technique that has overcome limitations of nuclear transformation, such as the low expression levels of recombinant proteins and transgene containment. A good example of the success of this technique is the high accumulation of the cryIIA protein, up to 47% of total cellular protein. Another advantage is that the presence of proteins in chloroplasts that facilitate posttranslational modifications, including the folding and assembly of prokaryotic and eukaryotic proteins. An example of this is the integration of the native Cholera Toxin B subunit into chloroplast genomes, and its assembly as functional oligomers was successfully achieved in transgenic tobacco chloroplast reaching an accumulation of 4.1% of total soluble protein.

One aspect of this invention is to create recombinant DNA vectors in order to enhance and show variable expression levels of the human IGF-1 protein via the plastid, and to study the difference in expression levels between the synthetic and the native human IGF-1 genes.

Unique to plants is the ability to regenerate whole plants from cells or tissues. This totipotency has many practical benefits: for example, plants propagated by seed can be cultured in vitro to yield thousands of identical plants (Bhojwani, 1990). In particular, tobacco is the easiest plant to genetically engineer and is widely used to test suitability of plant-based systems for bioproduction of recombinant proteins. Tobacco is an excellent biomass producer (in excess of 40 tons leaf fresh weight/acre based on multiple mowings per season) and a prolific seed producer (up to one million seeds produced per plant), thus hastening the time in which a product can be scaled up and brought to market (Cramer et al., 1998). In general, plant systems are more economical than industrial facilities using fermentation or bioreactor systems and the technology is already available for harvesting and processing plants and plant products on a large scale (Daniell et al., 2001a). Plant-derived products are less likely to be contaminated with human pathogenic microorganisms than those derived from animal cells because plants don't act as hosts for human infectious agents (Giddings et al., 2000).

Recombinant proteins expressed in plant cells are naturally protected from degradation when taken orally (Kong et al., 2001). Oral delivery is highly desirable for drug treatment (Gomez-Orellan and Paton, 1998).

The genetic information of plants is distributed among three cellular compartments: the nucleus, the mitochondria, and the plastids and each of these carries its own genome and expresses heritable traits (Bogorad, 2000). Transformation of the plant nucleus is routine in many species and there are a variety of techniques for delivering foreign DNA to the plant nuclear genome (Hager and Bock, 2000). However, recombinant protein expression in plants by nuclear transformation have been dismally low, with most levels much less than the 1% of total soluble protein that is needed for commercial feasibility if the protein must be purified (Daniell et al., 2002). Also incorporated by reference into this application is the utility application, based off of U.S. Provisional Application No. 60/393,651, and filed simultaneously with this application. Still another application, PCT/US02/41503, filed on Dec. 26, 2002, is also incorporated by reference into this application. In a general sense these applications describe in detail somatic embryogenosis for the construction of edible vaccines.

The plastids of plants are an attractive target for genetic engineering. Plant plastids (chloroplasts, amyloplasts, elaio-plasts, etioplasts, chromoplasts, etc.) are the major biosynthetic centers that, in addition to photosynthesis, are responsible for production of industrially important compounds such as amino acids, complex carbohydrates, fatty acids, and pigments. Plastids are derived from a common precursor known as a proplastid and thus the plastids present in a given plant species all have the same genetic content. In general, plant cells contain 500-10,0000 copies of a small 120-160 kilobase circular plastid genome, each molecule of which has a large (approximately 25 kb) inverted repeat. Thus, it is possible to engineer plant cells to contain up to 20,000 copies of a particular gene of interest which can result in very high levels of foreign gene expression.

The modern chloroplast of plants has retained a largely prokaryotic system of gene organization and expression, with the eukaryotic nuclear genome exerting significant regulatory control (Hager and Bock, 2000). Signaling pathways have evolved to coordinate gene expression between the chloroplast and the nuclear-cytosolic compartments during chloroplast development and in response to environmental factors such as light (Zerges, 2000). Illuminated chloroplasts possess extraordinarily high rates of transcription and translation that is tissue-specific due to regulation via untranslated regions of chloroplast-encoded mRNAs. Although communication between the chloroplast and the nucleus exist, these membrane-separated genetic systems have their own distinct environmental milieu containing different proteins, proteases and mechanisms of action. Unique features of the photosynthetic plastid enable genetic engineering of the chloroplast to overcome major limitations of plant nuclear transformation technology. One major concern with the genetic modification (GM) of plants is the possibility of the escape of foreign genes through pollen dispersal from transgenic plants to sexually compatible weedy relatives or to pathogenic microbes in the soil (Daniell, 2002). Such gene transfers could potentially result in the emergence of "superweeds" able to resist certain herbicides thereby undermining the benefits of GM crops (Daniell, 2002). However, genes in the chloroplasts of higher plants are generally transmitted only by the maternal parent, which means that chloroplast genes are not present in the pollen (Bogorad, 2000). Therefore, a foreign gene introduced by genetic engineering of the chloroplast genome could not transfer to genetically compatible weeds. This uniparental or maternal inheritance provides the gene containment necessary for keeping foreign genes sequestered in target plants and preventing gene flow among crops and weeds (Daniell, 2002).

Another remarkable feature of the plastid genome is its extremely high ploidy level: a single tobacco leaf cell may contain as many as 100 chloroplasts, each harboring approximately 100 identical copies of the plastid genome, resulting in an extraordinarily high ploidy degree of up to 10,000 plastid genomes per cell (Bogorad, 2000). Because of the very high ploidy level of the plastid genome, very high expression levels can be achieved. For example, the *Bacillus thuringiensis* (Bt) Cry2Aa2 protein accumulated as cuboidal crystals in transgenic chloroplasts and reached a level of 45.3% of the tsp in mature leaves (De Cosa et al., 2001).

For transformation of chloroplasts in plants, particle bombardment is used to introduce transgenes into leaf chloroplasts and stable transformation requires that all 10,000 chloroplast copies be uniformly converted (Bock and Hagemann, 2000). Securing genetically stable lines of plants with transgenic chloroplast requires every chloroplast to carry the inserted gene (Bogorad, 2000). This homoplasmic state is achieved through amplification and sorting of transgenic chloroplasts with the elimination of the wild-type copies on selective medium. The integration of cloned plastid DNA into the plastid genome occurs through site-specific homologous recombination in plants such as in tobacco *N. tabacum* and excludes the foreign vector DNA (Kavanagh et al., 1999). In contrast, nuclear transformation experiments in higher plants frequently suffer from epigenetic gene-silencing mechanisms resulting in inconsistent and unstable gene expression or complete loss of transgenic activity (Hager and Bock, 2000). The nuclear genome has mechanisms to effectively inactivate genes when regulatory sequences are inserted in a repetitive pattern and this occurs because integration of transgenes into the nuclear genome is random and through non-homologous recombination (Daniell and Dhingra, 2002). Random integrations of transgenes also means that the final location of the inserted gene may be in region of the nuclear genome that is not highly transcribed. As a consequence, nuclear expression levels vary in different transgenic lines and these differences are due the inserted gene's random position in the nuclear genome. Neither gene silencing nor position effects have been observed in genetically engineered chloroplasts (Daniell, and Dhingra, 2002).

Another major advantage of chloroplast engineering is the expression of multiple transgenes as operons due to efficient translation of polycistronic messenger RNAs (De Cosa et al., 2001). Genetic engineering has now moved from introducing single gene traits to coding for complete metabolic pathways, bacterial operons, and biopharmaceuticals that require assembly of complex multisubunit proteins (Daniell, 2002).

Disulfide bonds are common to many extracellular proteins because they stabilize the native conformation by lowering the entropy of the unfolded form (Abkevich and Shakhnovich, 2000). Most proteins need to be folded correctly for the protein to function properly and remain in solution. Eukaryotic secretory proteins are normally routed through the endoplasmic reticulum where disulfide bond formation occurs. Experiments show that chloroplasts have the machinery needed to fold complex eukaryotic secretory proteins in the soluble chloroplast stroma compartment. The activities of several chloroplast enzymes involved in the anabolic processes of carbon assimilation are enhanced or triggered by light through a signaling system called the ferredoxin-thioredoxin system (Ruelland and Miginiac, Maslow, 1999). Two correct disulfide bonds were formed in the tobacco chloroplast expression of human somatotropin (Staub et al., 2000). In another study, binding assays confirmed that chloroplast-synthesized cholera toxin of *Vibrio cholera* (CTB) bound intestinal receptors indicating that correct folding and disulfide bond formation had occurred (Daniell et al., 2001). The light signal sensed by chlorophyll is transferred via the photosynthetic electron flow to proteins called thioredoxins, which are very efficient in thio-disulfide interchanges with various protein disulfides (Ruelland and Miginiac-Maslow, 1999). Another mechanism for the simple, reversible activation of genes that regulate expression in the chloroplast is the Protein Disulfide Isomerase (PDI) system composed of chloroplast polyadenylate-binding proteins that specifically bind to the 5'UTR of the psbA mRNA and are modulated by redox status through PDI (Kim and Mayfield, 1997). The ability of chloroplasts to form disulfide bonds and properly fold foreign proteins eliminates a major part of the costly downstream processing.

Expression of functional human somatotropin in transgenic tobacco chloroplasts established that chloroplasts are capable of proper folding of human proteins with disulphide bonds (Staub et al., 2000). The ability to express multiple genes in a single transformation event (Daniell and Dhingra, 2002; De Cosa et al., 2001), accumulation of exceptionally large quantities of foreign proteins (De Cosa et al., 2001), successful engineering of tomato chromoplasts for high level transgene expression in fruits (Ruf et al., 2001, or carrots (Kumar et al., 2003), coupled to hyper-expression of vaccine antigens (Daniell et al., 2001b), and the use of plant derived antibiotic free selectable markers (Daniell et al., 2001c), augur well for oral delivery of edible vaccines and biopharmaceuticals that are currently beyond the reach of those who need them most. The term "edible vaccine" or "oral delivery" as used herein refers to a substance which may be given orally which will elicit a protective immunogenic response in a mammal.

Good recombinant systems are still not available for many human proteins that are expensive to purify or highly susceptible to proteolytic degradation. It is known that traditional purification of biopharmaceuticals proteins using columns accounts for 30% of the production cost and 70% of the set up cost (Petrides et al., 1995). Proteolytic degradation is another serious concern for industrial bioprocessing. The increasing production of proteins in heterologous hosts through the use of recombinant DNA technology has brought this problem into focus; heterologous proteins appear to be more prone to proteolysis (Enfors, 1992). Recombinant proteins are often regarded by a cell as foreign and therefore degraded much faster than most endogenous proteins (Rozkov et al., 2000). Proteolytic stability of recombinant proteins is a significant factor influencing the final yield. In view of these limitations, the Applicant has developed a more efficient method for producing a recombinant biopharmaceutical protein, such as IGF-1 production, which may be used as a model system to enrich or purify biopharmaceutical proteins from transgenic plants, which are highly susceptible to proteolytic degradation. It should be understood that when referring to IGF-1, the term included all variants of IGF-1 which are known in the art.

To date the no one has successfully transformed the plastid genome with IGF to create a delivery system that is easily administered and that stimulates both arms of the immune system without the severe side effects experienced by patients in current IGF treatments. In addition, until the Applicant's discovery, all production vehicles (*E. coli*, nuclear plant genomes, etc. . . . ) have failed to provide a cost effective and functional IGF, which can be orally administered without the side effects, i.e. human pathogens that are associated with the current production vehicles. In view of these limitations the Applicant developed a system for the expression of biopharmaceutical proteins, such as IGF, via the chloroplast genome in order to provide a feasible means of overproducing this increasingly useful therapeutic drug as well as addressing current concerns with the present methods of delivery and production.

SUMMARY OF THE INVENTION

One aspect of the invention is the creation of a plastid transformation vector for a stably transforming a plastid genome. The vector comprises, as operably-linked components, a first flanking sequence, a DNA sequence coding for a human insulin growth factor, which is capable of expression in said plastid genome, and a second flanking sequence. A second aspect provides a method for producing IGF. The method includes the steps of integrating the plastid transformation vector described above into the plastid genome of a plant cell, and then growing the plant cells to express IGF, and testing their functionality.

Still another aspect of the invention is an isolated and purified IFN derived from a chloroplast which has been transformed with the vector described above. Another aspect provides for an orally administrable therapeutic human interferon recombinant IFN, which is suitable for oral administration to a mammal. Yet another aspect of the invention provides for transformed plants, plant parts, plant cells and the progeny thereof, which are capable of expressing IGF. Yet another aspect is a synthetic IGF synthetic gene (IGF-1s) with a higher AT content as compared native IGF-1n gene. Still another aspect of this invention relates to the vector above described aspects, wherein IGF-1 is utilized.

BRIEF DESCRIPTION OF THE DRAWINGS

FIGS. 1A and 1B show the Nucleotide sequences of IGF-1 genes. FIG. 1A shows the nucleotide sequence of native IGF-1 gene (SEQ ID No 1). FIG. 1B shows the nucleotide sequence of synthetic IGF-1 gene (SEQ ID No. 2).

FIGS. 3A-3D show the diagrammatic representation of pLD5'UTR-ZZTEV-IGF-1 vectors and PCR confirmation of chloroplast integration. Two similar vectors were made, one with IGF-1n and the other with IGF-1s. The dotted lines show where the homologous recombination takes place. The primers 3P and 3M were used to confirm the integration of IGF-1 gene cassette into the chloroplast genome. FIG. 3A shows a diagrammatic representation of pLD5'UTR-ZZ-TEV-IGF-1 vectors. Transformed plants should produce a 1.65 kb PCR product. FIG. 3B shows a gel picture which illustrates different clones (lanes 1-3) that are transformed with IGF-1s gene cassette, lane 4 is the wild type. FIG. 3C shows the plants transformed with the IGF-1n (lanes 1-4) that show the 1.65 kb PCR product and lane 5 is the wild type tobacco plant (negative control). FIG. 3D shows Lanes 1 to 3 show different transgenic shoots that have integrated the 5'UTRZZTEVIGF-1s gene cassette. Lanes 4 to 6 show different transgenic shoots that have integrated the 5'UTRZZTEVIGF-1n gene cassette. Lane 7 shows the wild type plant (negative control).

FIG. 4A shows that if the transgenic plants are homoplasmic or hetoroplasmic. Lane 1 shows the wild type that has a hybridization fragment of 4.47 kb. Transgenic plants show two fragments, one of 5.2 kb and other of 930 bp. Lanes 2 and 3 are two different clones of 5'UTRZZTEVIGF-1s (T0). Lanes 4 and 5 show clones of the 5'UTRZZTEVIGF-1s (T1). Lanes 6 and 7 show the 5'UTRZZTEVIGF-1n clones (T0) and lane 8 shows the flanking sequence probe (positive control). FIG. 4B shows the transformed plants that contain the IGF-1 should show a 930 bp fragment. Lanes: 1—wild type, 2 & 3—IGF-1s-plants (T0), 4 &5—IGF-1s-plants (T1), 6 & 7—IGF-1n-plants, 8—blank, and 9—the IGF-1 probe was used as a positive control.

FIG. 5A shows the map of pLD-5'UTR-ZZTEVIGF-1 shows a monocistron transcript of 1099 nt, a dicistron transcript of 2019 nt, and polyciston transcript of 4519 nt. FIG. 5B shows that lane 1 is the untransformed plant. Lanes 2 and 3 are the 5'UTRZZTEVIGF-1s clones (T0). Lanes 4 to 7 are clones of the 5'UTRZZTEVIGF-1s (T1). Lanes 8 and 9 are the 5'UTRZZTEVIGF-1n clones (T0). Lane 10 is blank and in lane 11 the IGF-1 probe was used as a positive control. All the transgenic plants are transcribing the IGF-1 gene and the most abundant transcript is the monocistron.

FIG. 7A shows that the Plant grew in a 16 hours light and 8 hours dark photoperiod. FIG. 7B shows that the plants were exposed to continuous light for 13 days and the plant samples were collected at different times. The IGF-1 expression is shown as a percentage of total soluble protein. FIG. 7C shows the Protein quantification by ELISA in young (Y), mature (M), and old transgenic leaves (O). The highest amount of IGF-1 is found in the mature leaves, and the IGF-1 protein expression decreases in the older leaves. FIG. 7D shows the Protein quantification by ELISA in seedling and potted plants. ELISA shows that IGF-1 expression levels increase with continued growth. FIG. 7E shows the IGF-1 expression levels in the T0 and T1 in the plants transformed with the IGF-1s. FIG. 7F shows the total and soluble fractions in IGF-1s in T1 and T0 generations.

DETAILED DESCRIPTION OF INVENTION

Figure 2:
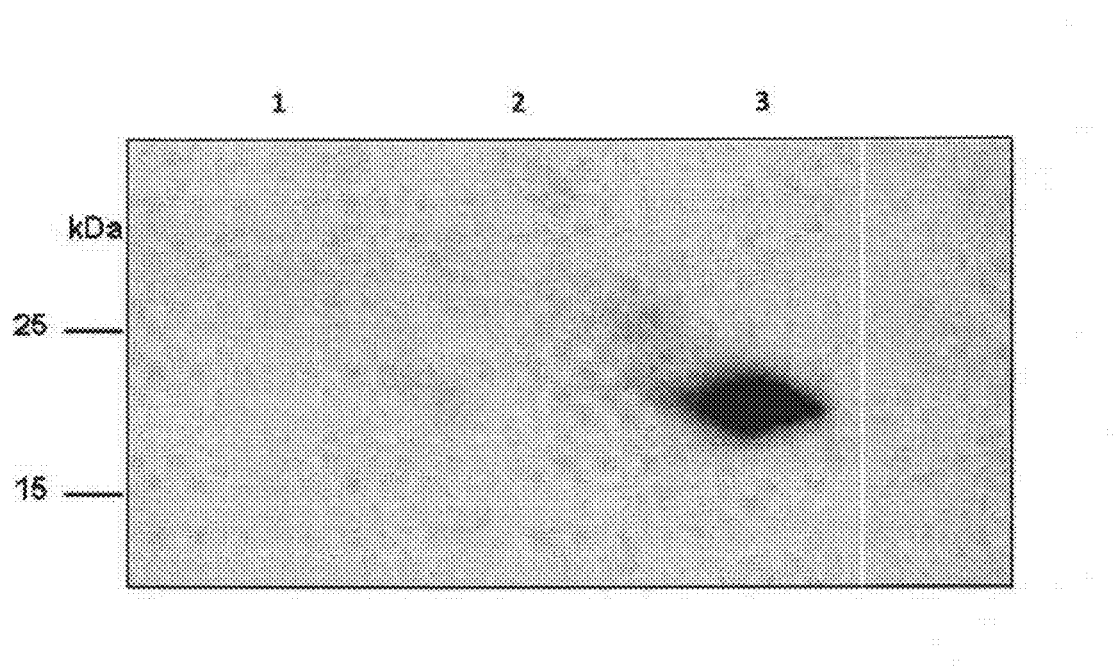
FIG. 2 shows the IGF-1 Expression in *E. coli*. Western blots were detected using mouse anti-human IGF-1. Lanes: 1—untransformed *E. coli*, 2—pLD5'UTRZZTEVIGF-1n, 3—pLD5'UTRZZTEVIGF-1s. The zz tag-TEV-IGF-1 polypeptide has a molecular size of approximately 24 kDa.

In one preferred embodiment, vectors are provided, which can be stably integrated into the plastid genome of plants for the variable-expression of Human Serum Albumin (HSA). In other preferred embodiments methods of transforming plastid genomes to variable-express HSA, transformed plants and progeny thereof, which variable-express HSA are provided. Still another embodiment provides for methods of variable-expressing biopharmaceutical proteins using selected regulatory elements. Another embodiment provides for methods and constructs which protect biopharmaceutical proteins from proteolytic degradation.

The preferred aspects of this application are applicable to all plastids of higher plants. These plastids include the chromoplasts, which are present in the fruits, vegetables, and flowers; amyloplasts which are present in tubers such as potato; proplastids in the roots of higher plants; leucoplasts and etioplasts, both of which are present in the non-green parts of plants.

DEFINITIONS

To better understand the current disclosure, the following definitions, which shall hold their meaning throughout this application unless otherwise noted, are provided to put the application in proper context.

Variable-expression should be understood to mean the expression of HSA which yields variable amounts of HSA per gram of fresh weight of transgenic plants.

Properly folded should be understood to mean a protein that is folded into its normal conformational configuration, which is consistent with how the protein folds as a naturally occurring protein expressed in its native host cell.

Substantially homologous as used throughout the ensuing specification and claims, is meant a degree of homology to the native IGF-1 sequence in excess of 50%, most preferably in excess of 80%, and even more preferably in excess of 90%, 95% or 99%. Substantial sequence identity or substantial homology as used herein, is used to indicate that a nucleotide sequence or an amino acid sequence exhibits substantial structural or functional equivalence with another nucleotide or amino acid sequence. Any structural or functional differences between sequences having substantial sequence identity or substantial homology will be de minimis; that is, they will not affect the ability of the sequence to function as indicated in the desired application. Differences may be due to inherent variations in codon usage among different species, for example. Structural differences are considered de minimis if there is a significant amount of sequence overlap or similarity between two or more different sequences or if the different sequences exhibit similar physical characteristics even if the sequences differ in length or structure. Such characteristics include, for example, ability to maintain expression and properly fold into the proteins conformational native state, hybridize under defined conditions, or demonstrate a well defined immunological cross-reactivity, similar biopharmaceutical activity, etc. Each of these characteristics can readily be determined by the skilled practitioner in the art using known methods.

Spacer region is understood in the art to be the region between two genes. The chloroplast genome of plants contains spacer regions which highly conserved nuclear tide sequences. The highly conserved nature of the nuclear tide sequences of these spacer regions chloroplast genome makes the spacer region ideal for construction of vectors to transform chloroplast of a wide variety of plant species, without the necessity of constructing individual vectors for different plants or individual crop species. It is well understood in the art that the sequences flanking functional genes are well-known to be called "spacer regions". The special features of the spacer region are clearly described in the Applicant's application Ser. No. 09/079,640 with a filing date of May 15, 1998 and entitled UNIVERSAL CHLOROPLAST INTEGRATION OF EXPRESSION VECTORS, TRANSFORMED PLANTS AND PRODUCTS THEREOF. The aforementioned application Ser. No. 09/079,640 is hereby incorporated by reference. It was well-known that there are at least sixty transcriptionally-active spacer regions within the higher plant chloroplast genomes (Sugita, M., Sugiura. M., Regulation of Gene Expression in Chloroplasts of Higher Plants, *Plant Mol. Biol.*, 32: 315-326, 1996). Specifically, Sugita et al. reported sixty transcriptionally-active spacer regions referred to as transcription units, as can be seen in Table II of the article. Because the transcriptionally active spacer regions are known, a universal vector, as described in the Applicant's U.S. patent application Ser. No. 09/079,640, can be used in the identified spacer regions contained within a variety of the higher plant chloroplast genomes. By utilizing the teachings in Sugita et al., intergenic spacer regions are easily located in the plastid genome. Consequently this allows one skilled in the art to use the methods taught in the Applicant's U.S. patent application Ser. No. 09/079,640 to insert a universal vector containing the psbA, the 5' untranslated region (UTR) of psbA and the gene coding for HSA into the spacer regions identified by Sugita et al., and found across higher plants. The aforementioned applications and article are incorporated by reference.

Selectable marker provides a means of selecting the desired plant cells, vectors for plastid transformation typically contain a construct which provides for expression of a selectable marker gene. Marker genes are plant-expressible DNA sequences which express a polypeptide which resists a natural inhibition by, attenuates, or inactivates a selective substance, i.e., antibiotic, herbicide, or an aldehyde dehydrogenase such as Betaine aldehyde dehydrogenase (described in the Applicant's application Ser. No. 09/807,722 filed on Apr. 18, 2001, and herein fully incorporated by reference). Alternatively, a selectable marker gene may provide some other visibly reactive response, i.e., may cause a distinctive appearance or growth pattern relative to plants or plant cells not expressing the selectable marker gene in the presence of some substance, either as applied directly to the plant or plant cells or as present in the plant or plant cell growth media.

In either case, the plants or plant cells containing such selectable marker genes will have a distinctive phenotype for purposes of identification, i.e., they will be distinguishable from non-transformed cells. The characteristic phenotype allows the identification of cells, cell groups, tissues, organs, plant parts or whole plants containing the construct. Detection of the marker phenotype makes possible the selection of cells having a second gene to which the marker gene has been linked.

The use of such a marker for identification of plant cells containing a plastid construct has been described in the literature. In the examples provided below, a bacterial aadA gene is expressed as the marker. Expression of the aadA gene confers resistance to spectinomycin and streptomycin, and thus allows for the identification of plant cells expressing this marker. The aadA gene product allows for continued growth and greening of cells whose chloroplasts comprise the selectable marker gene product. Numerous additional promoter regions may also be used to drive expression of the selectable marker gene, including various plastid promoters and bacterial promoters which have been shown to function in plant plastids.

Inverted Repeat Regions are regions of homology, which are present in the inverted repeat regions of the plastid genome (known as IRA and IRB), two copies of the transgene are expected per transformed plastid. Where the regions of homology are present outside the inverted repeat regions of the plastid genome, one copy of the transgene is expected per transformed plastid.

Structural equivalent should be understood meaning a protein maintaining the conformational structure as the native protein expressed in its natural cell.

Vectors

The current application contemplates the use of vectors capable of plastid transformation, particularly of chloroplast transformation. Such vectors include chloroplast expression vectors such as pUC, pBR322, pBLUESCRIPT, pGEM, and all others identified by Daniel in U.S. Pat. No. 5,693,507 and U.S. Pat. No. 5,932,479. Included are also vectors whose flanking sequences are located outside of the embroidered repeat of the chloroplast genome: These publications and patents are hereby incorporated by reference to the same extent as if each individual publication or patent was specifically an individually indicated to be incorporated by reference.

The preferred embodiment of this invention utilizes the universal integration and expression vector competent for stably transforming the plastid genome of different plant species (universal vector). The universal vector is described in WO 99/10513 which was published on Mar. 4, 1999, and application Ser. No. 09/079,640 which was filed on May 15, 1998, wherein both of said references are incorporated in their entirety.

The vectors can be constructed with different promoters as was described in U.S. patent application Ser. No. 09/079,640, different selectable markers such as those described in U.S. patent application Ser. No. 09/807,722, and different flanking sequences suitable for integration into a variety of plant plastid genomes.

General Methodology for Transforming the Plastid Genome

This illustrative example shows generally all of the necessary steps to practice the Applicants invention. Of course other suitable methods, which are known in the art may be substituted or used to supplement the example methodology described herein.

Isolation of Genomic DNA from Plants.

Mortar and pestle, liquid nitrogen, fresh dark green leaves. DNeasy Plant Mini Kit (QIAGEN Inc.)

PCR Amplification of Chloroplast Flanking Sequence.

Materials for PCR reaction: Genomic DNA (50-100 ng/µl), dNTPs, 10× pfu buffer, Forward primer, Reverse primer, autoclaved distilled $H_2O$ and Turbo pfu DNA Polymerase.

Vector Construction.

1. Plasmid pUC19 or pBlueScript SK (+/−).
2. Species specific PCR amplified chloroplast DNA flanking sequences.
3. A promoter functional in plastids, 5'UTR of chloroplast gene, selectable marker gene, gene of interest and chloroplast 3'UTR.

4. Restriction enzymes and buffers.
5. T4 DNA polymerase to remove 3' overhangs to form blunt ends and fill-in of 5' overhangs to form blunt ends or Klenow large fragment (fill-in of 5' overhangs to form blunt ends), alkaline phosphatase for dephoshorylation of cohesive ends, DNA ligase to form phosphodiester bonds and appropriate buffers.
6. Water baths or incubators set at different temperatures.

Preparation for Biolistics.
1. Autoclaved Whatman filter paper #1 (55 mm in diameter) dried in oven.
2. 100% ethanol.
3. Autoclaved tips in box, autoclaved kimwipes tissues wrapped in aluminum foil.
4. Sterile gold particles stored at −20° C. in 50% glycerol (see Notes 1 and 2).
5. Sterile rupture discs (1100 psi) and macrocarriers sterilized by dipping in 100% ethanol.
6. Autoclaved steel macrocarrier holders and stopping screens.
7. Freshly prepared 2.5 mM $CaCl_2$: weigh 1.84 g and dissolve in 5 mL $H_2O$ and filter sterilized with 0.2 μm filter.
8. 0.1 M spermidine (highly hygroscopic): dilute 1M spermidine stock to 10× and aliquot 100 μL in 1.5 mL Eppendrop tubes to store at −20° C. Discard each tube after single use.

Medium Preparation for Plant Tissue Culture.
2.5.1. Tobacco.
Medium for 1000 mL: 4.3 g MS salts (INVITROGEN Inc.), $H_2O$ (molecular biology grade), 100 mg/L myo-inositol, 1 mg/L thiamine-HCl, 3% sucrose for shoot induction and 2% sucrose for root induction, 1 mg/L 6-benzyl aminopurine (BAP; use 1 mL from 1 mg/mL stock), 0.1 mg/L indole-3-acetic acid (use 0.1 mL from 1 mg/mL IAA stock), 1 mg/L indole-3-butyric acid for root induction (use 1 mL from 1 mg/mL IBA stock). Add 500 mg/L spectinomycin in autoclaved medium when it cools to 45° C.-50° C. (use 5 mL filter sterilized spectinomycin from 100 mg/mL stock).

Edible Crops.
Potato.
Medium for 1000 mL: 4.3 g MS salts, B5 vitamins (make 100× solution in 100 mL $H_2O$ by dissolving: 1 g myo-inositol, 10 mg nictonic acid, 10 mg pyridoxine-HCl, 100 mg thiamine-HCl; use 10 mL, store remaining solution at 4° C.), 5 mg/l zeatin riboside (use 0.5 mL from 1 mg/mL ZR stock), 0.1 mg/l α-napthaleneacetic acid (use 0.1 mL from 1 mg/mL NAA stock), 40 to 500 mg/L spectinomycin.

Tomato
Medium for 1000 mL: 4.3 g MS salts, B5 vitamins (10 mL from 10× stock), 0.2 mg/l indole-3-acetic acid (use 0.2 mL from 1 mg/mL IAA stock), 3 mg/l of 6-benzylaminopurine (use 3 mL from 1 mg/mL BAP stock). 300 or 500 mg/L spectinomycin.

For all plant growth media adjust to pH 5.8 with 1N KOH or 1N NaOH and add 6 g/L phytagel (Sigma) before autoclaving at 121° C. for 20 min. For preparation of 1 mg/mL stock of BAP, IAA, IBA, NAA, ZR respectively: weigh 10 mg powder and dissolve first in 1 or 2 drops of 1N NaOH and make up the final volume to 10 mL; store all plant growth regulators at 4° C. for 1-2 months).

Molecular Analysis of Transgenic Plants.
PCR Analysis for Gene Integration into Tobacco Chloroplasts
PCR reaction for 50 μL: 1.0 μL genomic DNA (50-100 ng/μl), 1.5 μl dNTPs (stock 10 mM), 5.0 μl (10× PCR buffer), 1.5 μl Forward primer (to land on the native chloroplast genome; stock 10 μM), 1.5 μl Reverse primer (to land on the transgene; stock 10 μM), 39.0 μl autoclaved distilled $H_2O$ and 0.5 μl Taq DNA polymerase.

Analysis of Homoplasmy by Southern Blots.
1. Depurination solution: 0.25 N HCl (use 0.4 mL HCl from 12.1 N HCl; Fisher Scientific USA, to make up final volume 500 mL with distilled $H_2O$).
2. Transfer buffer: 0.4 N NaOH, 1 M NaCl (weigh 16 g NaOH and 58.4 g NaCl and dissolve in distilled $H_2O$ to make up the final volume to 1000 mL).
3. 20×SSC: 3M NaCl, 0.3 M sodium citrate trisodium salt (weigh 175.3 g NaCl, 88.2 g $Na_3C_6H_5O_7.2H_2O$ 900 mL $H_2O$ and adjust pH 7.0 using 1 N HCl and make up the final volume to 1000 mL with distilled $H_2O$ and autoclave).
4. 2×SSC: Add 20 mL of 20×SSC in 180 mL of distilled $H_2O$.

Protein Analysis by Western Blots.
1. Acrylamide/Bis: ready made from Fischer (USA), stored at 4° C.
2: 10% SDS: dissolve 10 g SDS in 90 mL deionized water, make up the volume to 100 mL, store at room temperature.
3. Resolving gel buffer: 1.5 M Tris-HCl (add 27.23 g Tris base in 80 mL water, adjust to pH 8.8 with 6 N HCl and make up the final volume to 150 mL. Store at 4° C. after autoclaving);
4. Stacking gel buffer: 0.5 M Tris-HCl (add 6.0 g Tris base in 60 mL water. Adjust to pH 6.8 with 6 N HCl. Make up the volume to 100 mL. Store at 4° C. after autoclaving).
5. Sample Buffer (SDS Reducing Buffer): In 3.55 mL water add 1.25 mL 0.5 M Tris-HCl (pH 6.8), 2.5 mL glycerol, 2.0 mL (10% SDS), 0.2 mL (0.5% Bromophenol blue). Store at room temperature. Add 50 μL β-Mercaptoethanol (βME) to 950 μL sample buffer prior to its use.
6. 10× running buffer (pH 8.3): Dissolve 30.3 g Tris Base, 144.0 g Glycine and 10.0 g SDS in ~700 mL water (add more water if not dissolving). Bring up the volume to 1 L and store at 4° C.
7. 10× PBS: Weigh 80 g NaCl, 2 g KCl, 26.8 g $Na_2HPO_4^{-7}$ $H_2O$ (or 14.4 g $Na_2HPO_4$), 2.4 g $KH_2PO_4$ in 800 mL water. Adjust pH to 7.4 with HCl and make up the volume to 1 L. Store at room temperature after autoclaving.
8. 20% APS: Dissolve 200 mg ammonium persulfate in 1 mL water (make fresh every two weeks).
9. Transfer buffer for 1500 mL: Add 300 mL 10× running buffer, 300 mL methanol, 0.15 g SDS in 900 mL water and make volume to 1 L.

Plant Extraction Buffer:

|  | Used Concentration | Final Concentration |
| --- | --- | --- |
| 60 μl | 5M NaCl | 100 mM |
| 60 μl | 0.5M EDTA | 10 mM |
| 600 μl | 1M Tris-HCl | 200 mM |
| 2 μl | Tween-20 | .05% |
| 30 μL | 10% SDS | 0.1% |
| 3 μL | BME | 14 mM |
| 1.2 mL | 1M Sucrose | 400 mM |
| 1 mL | Water | |
| 60 μL | 100 mM PMSF | 2 mM |

Add PMSF just before use (vortex to dissolve PMSF crystals).

PMSF (Phenylmethyl sulfonyl fluoride): Dissolve 17.4 mg of powdered PMSF in 1 mL of methanol by vortexing and store at −20° C. for up to a month.

Methods

Isolation of Genomic DNA from Plants.

Extract the genomic DNA from fresh green leaves using DNeasy Plant kit (QIAGEN Inc.) following vender's instructions.

Amplification of Chloroplast Flanking Sequence.

Species-specific flanking sequences from the chloroplast DNA or genomic DNA of a particular plant species is amplified with the help of PCR using a set of primers that are designed using known and highly conserved sequence of the tobacco chloroplast genome.

Conditions for running PCR reaction: There are three major steps in a PCR, which are repeated for 30 to 40 cycles. (1) Denaturation at 94° C.: to separate double stranded chloroplast DNA. (2) Annealing at 54 to 64° C.: primers bind to single stranded DNA with formation of hydrogen bonds and the DNA polymerase starts copying the template. (3) Extension at 72° C.: DNA Polymerase at 72° C. extends to the template that strongly forms hydrogen bond with primers. Mismatched primers will not form strong hydrogen bonds and therefore, all these temperatures may vary based on DNA sequence homology. The bases complementary to the template are coupled to the primer on the 3' side. The polymerase adds dNTPs from 5' to 3', reading the template in 3' to 5' direction and bases are added complementary to the template.

Chloroplast Transformation Vector.

The left and right flanks are the regions in the chloroplast genome that serve as homologous recombination sites for stable integration of transgenes. A strong promoter and the 5' UTR and 3' UTR are necessary for efficient transcription and translation of the transgenes within chloroplasts. For multiple gene expression, a single promoter may regulate the transcription of the operon, and individual ribosome binding sites must be engineered upstream of each coding sequence (2) (FIG. 10). The following steps are used in vector construction:

1. Amplification of flanking sequences of plastid with primers that are designed on the basis of known sequence of the tobacco chloroplast genome (between 16S-23S region of chloroplast).
2. Insert the PCR product containing the flanking sequence of the chloroplast genome into pUC19 plasmid digested with PvuII restriction enzyme (to eliminate the multiple cloning site), dephoshorylated with the help of alkaline phosphatase (CIP) for 5 min at 50° C. (to prevent recircularization of cloning vector). Inactivate CIP enzyme at 68° C. for 10 min.

Clone chloroplast transformation cassette (which is made blunt with the help of T4 DNA polymerase or Klenow filling) into a cloning vector digested at the unique PvuII site in the spacer region, which is conserved in all higher plants examined so far.

Delivery of Foreign Genes into Chloroplasts Via Particle Gun.

This is most successful and a simple technique to deliver transgenes into plastids and is referred as Biolistic PDS-1000/He Particle Delivery System (18,19). This technique has proven to be successful for delivery of foreign DNA to target tissues in a wide variety of plant species and integration of transgenes has been achieved in chloroplast genomes of tobacco (2), *Arabidopsis* (20), potato (21), tomato (25) and transient expression in wheat (22), carrot, marigold and red pepper (23) (see Note 5).

Preparation of Gold Particle Suspension.

1. Suspend 50-60 mg gold particles in 1 mL 100% ethanol and vortex for 2 min.
2. Spin at maximum speed ~10,000×g (using tabletop microcentrifuge) for 3 min.
3. Discard the supernatant.
4. Add 1 ml fresh 70% ethanol and vortex for 1 min.
5. Incubate at room temperature for 15 min and shake intermittently.
6. Spin at 10,000×g for 2 min.
7. Discard supernatant, add 1 ml sterile distilled $H_2O$, vortex for 1 min, leave at room temperature for 1 min, and spin at 10,000×g for 2 min.
8. Repeat above washing process three times with $H_2O$ (step 7).
9. Resuspend the gold-pellet in 1 mL 50% glycerol, store stock in −20° C. freezer.

Precipitation of the chloroplast vector on gold particles for five samples.

1. Take 50 µl the gold particles in 1.5 mL tube after vortexing for a 1 min.
2. Add 10 µl DNA (about 1 µg/µl plasmid DNA), and vortex the mixture for 30 sec.
3. Add 50 µl of 2.5 M $CaCl_2$ and vortex the mixture for 30 sec.
4. Add 20 µl of 0.1 M spermidine and vortex the mixture for 20 min at 4° C.

Washing of Chloroplast Vector Coated on Gold Particles.

1. Add 200 µl 100% ethanol and vortex for 30 sec.
2. Spin at 3000×g for 40 sec.
3. Pour off ethanol supernatant.
4. Repeat ethanol washings five times.
5. In the last step, pour off ethanol carefully and add 35-40 µl ethanol (100%).

Preparation of Macrocarriers.

1. Sterilize macrocarriers by dipping in 100% ethanol for 15 min and insert them into sterile steel ring holder with the help of a plastic cap when air-dried.
2. Vortex the gold-plasmid DNA suspension and pipet 8-10 µl in the center of macrocarrier and let it air dry.

Gene Gun Setup for Bombardment of Samples.

1. Wipe the gun chamber and holders with 100% ethanol using fine tissue paper (do not wipe the door with alcohol).
2. Turn on the vacuum pump.
3. Turn on the valve (Helium pressure regulator) of Helium gas tank (anti-clockwise).
4. Adjust the gauge valve (adjustable valve) ~200 to 250 psi above the desired rupture disk pressure (clockwise) using adjustment handle.
5. Turn on the gene gun.
6. Place the rupture disc (sterilized by dipping in 100% ethanol for 5 min) in the rupture disc-retaining cap and tightly screw to the gas acceleration tube.
7. Place a stopping screen in the macrocarrier launch assembly and above that place macrocarrier with gold particles with chloroplast vector facing down towards screen. Screw assembly with a macrocarrier coverlid and insert in the gun chamber.
8. Place an intact leaf or explants to be bombarded on a filter paper (Whatman No. 1) soaked in medium containing no antibiotics. Place sample plate over target plate shelf, insert in the gun chamber and close the bombardment chamber door.
9. Press Vac switch to build pressure (up to 28 inches of Hg) in the vacuum gauge display. Turn same switch down at hold point and press Fire switch until you hear a burst sound of the ruptured disc.
10. Press Vent switch to release the vacuum and open the chamber to remove sample.

11. Shut down the system by closing the main valve (Helium pressure regulator) on the Helium gas cylinder. Create some vacuum in the gene gun chamber and keep using fire switch on and off until both pressure gauges' show zero reading. Release the vacuum pressure and turn off the gene gun and vacuum pump.
12. Incubate bombarded sample plates in the culture room for two days in the dark (i.e. covered with aluminum foil) and on the third day cut explants in appropriate pieces and place on the selection medium.

Plant Tissue Culture and Chloroplast Transformation.

Tobacco Chloroplast Transformation.

A highly efficient and reproducible protocol has been established for Nicotiana tabacum cv. Petit Havana (Daniell, H. (1997) Methods in Mol. Biol. Recombinant gene expression protocols. 62, 463-489.

1. Bombard 4 weeks old dark green tobacco leaves on the abaxial (bottom side) side with the chloroplast vector and incubate leaves in the dark for 2 days on selection free medium.
2. On the third day cut bombarded leaf explants into small square pieces (5 mm) and place explants facing abaxial surface towards selection medium containing MS salts, 1 mg/l thiamine HCl, 100 mg/l myo-inositol, 3% sucrose, 1 mg/l BAP and 0.1 mg/l IAA along with 500 mg/l spectinomycin as a selective agent.
3. Transgenic shoots should appear after three to five weeks of transformation. Cut the shoot leaves again into small square explants (2 mm) and subject to a second round of selection for achieving homoplasmy on fresh medium.
4. Regenerate transgenic shoots (confirmed by PCR for transgene integration) on rooting medium containing MS salts, 1 mg/l thiamine HCl, 100 mg/l myo-inositol, 2% sucrose and 1 mg/l IBA with 500 mg/l spectinomycin.
5. Transfer transgenic plants into pots under high humidity and move them to green house or growth chamber for further growth and characterization.

Plastid Transformation of Edible Crops.

The concept of universal vector for using the chloroplast DNA from one plant species to transform another species (of unknown sequence) was developed by the Daniell group (8). Using this concept both tomato and potato chloroplast genomes were transformed as described below.

Potato Chloroplast Transformation.

Using the tobacco chloroplast vector, leaf tissues of potato cultivar FL1607 was transformed via biolistics, and stable transgenic plants were recovered using the selective aadA gene marker and the visual green fluorescent protein (GFP) reporter gene (21).

1. Bombard potato leaves (3-4 week old) and incubate in the dark for 2 days on selection free medium.
2. Third day excise leaves into small square pieces (5 mm) and place on MS medium containing B5 vitamins, 5 mg/l ZR, 0.1 NAA, and 3% sucrose. Gradually increase spectinomycin selection pressure (40 to 400 mg/l) after every two weeks subculture under diffuse light.
3. Regenerate shoots from transgenic potato calli on MS medium containing B5 vitamins, 0.01 mg/L NAA, 0.1 mg/L GA3, 2% sucrose and 40-400 mg/l spectinomycin.
4. Transfer transgenic shoots on basal MS medium containing B5 vitamins, 2% sucrose and 40-400 mg/l spectinomycin for root induction. Transfer transgenic plantlets to growth chamber.

Tomato Chloroplast Transformation.

Using the tobacco chloroplast vector, tomato (Lycopersicon esculentum cv. IAC Santa Clara) plants with transgenic plastids were generated using very low intensity of light (25).

1. Bombard four-week-old tomato leaves and incubate in the dark for 2 days on selection free medium.
2. Excise bombarded leaves into small pieces and place on shoot induction medium containing 0.2 mg/L IAA, 3 mg/L BAP, 3% sucrose and 300 mg/L spectinomycin.
3. Select spectinomycin-resistant primary calli after a three to four month duration without any shoot induction.
4. Regenerate shoots in about four weeks after transfer of transgenic calli to shoot induction medium containing 0.2 mg/L IAA, 2 mg/L ZR, 2% sucrose and 300 mg/L spectinomycin then root on hormone-free medium. Transfer regenerated transgenic plants into the greenhouse.

Molecular Analysis of Transgenic Plants.

PCR Screening of Transgenic Shoots.

This method has been used to distinguish between mutants, nuclear and chloroplast transgenic plants. By landing one primer on the native chloroplast genome adjacent to the point of integration and a second primer on the aadA gene (26. PCR product of an appropriate size should be generated in chloroplast transformants. Since this PCR product cannot be obtained in nuclear transgenic plants or mutants, the possibility of nuclear integration or mutants should be eliminated.

1) Extract the genomic DNA from transgenic leaf tissue using DNeasy Plant kit (QIAGEN Inc.) by following vender's instructions. For lower amount of transgenic tissues, volume of buffers may be reduced appropriately.
2) Run PCR reaction with Taq DNA Polymerase (QIAGEN Inc.) using appropriate primers following the same conditions as described above for amplification of flanking sequences.

Analysis of Homoplasmy by Southern Blot.

In Southern blot analysis, tobacco plastid genome digested with suitable restriction enzymes should produce a smaller fragment (flanking region only) in wild type plants compared to transgenic chloroplast that include transgene cassette as well as the flanking region. In addition, homoplasmy in transgenic plants is achieved when only the transgenic fragment is observed.

Transfer of DNA to Membrane.

1. Digest the genomic DNA (~2 to 10 μg) with suitable restriction enzymes from transgenic samples (including wild type as a control) and run digested DNA on 0.8% agarose gel containing 5 μL EtBr (from 10 mg/mL stock) in 100 mL for four hours at 40V.
2. Soak gel in 0.25 N HCl (depurination solution) for 15 minutes and rinse gel twice in distilled $H_2O$ for 5 minutes.
3. Soak gel for 20 minutes in transfer buffer to denature DNA.
4. Transfer overnight DNA from gel to nylon membrane (pre-soak first in water, then in transfer buffer for 5 minutes) using the transfer buffer.
5. Next day, rinse membrane twice with 2×SSC buffer for 5 minutes each and air-dry for 5 minutes on filter papers. Cross-link transferred DNA to membrane using GS GeneLinker UV Chamber (Bio-Rad) at appropriate (C3) setting.

Preparation of Probe.

1. Digest any plasmid (containing flanking sequences of the chloroplast genome) with appropriate restriction enzymes.

2. Denature 45 µL flanking DNA fragment (50-250 ng) at 95° C. for 5 minutes, then place on ice for 2-3 minutes.
3. Add denatured probe to Ready-To-Go DNA Labeling Beads (–dCTP) tube (Amersham Biosciences, USA) and gently mix by flicking the tube.
4. Add 5 µL radioactive $\alpha^{32}P$ (dCTP; Amersham Biosciences, USA) to probe mixture and incubate at 37° C. for 1 hour and filter the probe using ProbeQuant G-50 Micro Columns (Amersham Pharmacia Biotech Inc. USA).

Prehybridization and Hybridization.

Place the blot (DNA transfer side facing towards the solution) in a hybridization bottle and add 10 mL Quik-Hyb (Stratagene, USA).

Incubate for 1 hour at 68° C. Add 100 µL sonicated salmon sperm (10 mg/mL stock; Stratagene, USA) to the labeled probe and heat at 94° C. for 5 minutes and add to bottle containing membrane and Quik-Hyb solution. Incubate for 1 hour at 68° C.

Washing and Autoradiography.
1. Discard Quik-Hyb solution with probe and wash membrane twice in 50 mL (2×SSC buffer and 0.1% SDS) for 15 minutes at room temperature.
2. Wash membrane twice in 50 mL (0.1×SSC buffer and 0.1% SDS) for 15 minutes at 60° C.
3. Wrap the wash membrane in saran wrap and expose blot to x-ray film in the dark and leave at –70° C. until ready for development.

Determination of Transgene Expression by Western Blot.

Extraction of Plant Protein.
1. Grind 100 mg of leaf in liquid nitrogen and add 200 µL of extraction buffer to samples on ice.
2. Add appropriate volume of freshly prepared 2× Sample loading buffer to an aliquot plant extract (from a stock containing 50 µL β-mercaptoethanol and 950 µL sample loading buffer).
3. Boil samples for 4 minutes with loading dye and centrifuge for 2 minutes at 10,000×g, then immediately load 20 µL samples into gel.

Running Gel.

Load samples on gel and run for half hour at 100 V, then 1 hour at 150 V until the marker bands corresponding to your protein are in middle.

Transfer of Protein to Membrane.

Transfer protein from gel to membrane using Mini Transfer Blot Module at 30 V overnight or 65 V for 2 hours or 100 V for 1 hour. Membrane wrapped in saran wrap can be stored at –20° C. for a few days if necessary.

Membrane Blocking
1. After transfer, rinse membrane with water and incubate membrane in PTM (100 mL 1×PBS, 50 µL 0.05% Tween 20, and 3 g dry milk (3%) for 1 hour at room temperature.
2. Add primary antibody in suitable dilution for 15 mL and incubate for 2 hours at room temperature. Wash membrane twice with 1×PBS for 5 minutes each.
3. Add secondary antibody in proper dilution for 20 mL. Incubate for 1.5 hours at room temperature on a shaker.
4. Wash twice with PT (100 ml 1×PBS+50 µL Tween 20) for 15 minutes and finally with 1×PBS for 10 minutes.

Exposure of the Blot to X-Ray Film.
1. Mix 750 µL of each chemiluminescent solution (Luminol Enhancer and Stable Peroxide) in 1.5 mL tube and add to membrane, cover thoroughly.
2. Wipe out extra solution and expose blot to x-ray film for appropriate duration and develop film.

Seed Sterilization.
1. Vortex small amount of seeds into microcentrifuge tube with 1 mL 70% ethanol for 1 minute. Discard ethanol after brief spin.
2. Add 1 mL disinfecting solution (1.5% Bleach and 0.1% Tween 20) in tube and vortex intermittently for 15 min. Discard solution after brief spin.
3. Wash the seed thrice with sterile distilled water.
4. Spray seeds with sterile water on plate containing RMOP basal medium supplemented with 500 µg/mL spectinomycin to determine maternal inheritance in transgenic chloroplast plants.

Evaluation of Results.

Maternal Inheritance in Chloroplast Transgenic Plants.

Transgenes integrated into chloroplast genomes are inherited maternally. This is evident when transgenic seed of tobacco are germinated on RMOP basal medium containing 500 µg/mL spectinomycin. There should be no detrimental effect of the selection agent in transgenic seedlings whereas untransformed seedlings will be affected.

CTB-GM1-Gangliosides Binding ELISA Assay.
1. Coat microtiter plate (96 well ELISA plate) with monosialoganglioside-GM1 {3.0 µg/mL in bicarbonate buffer (15 mM $Na_2CO_3$, 35 mM $NaHCO_3$, pH 9.6)} and as a control, coat BSA (3.0 ug/mL in bicarbonate buffer) in few wells.
2. Incubate plate overnight at 4° C.
3. Block wells with 1% (w/v) bovine serum albumin (BSA) in 0.01 M phosphate-buffered saline (PBS) for two hours at 37° C.
4. Wash wells thrice with PBST buffer (PBS containing 0.05% Tween 20).
5. Incubate plate by adding soluble protein from transformed and untransformed plants and bacterial CTB in PBS.
6. Add primary antibodies (rabbit anti cholera serum diluted 1:8000 in 0.01 M PBST containing 0.5% BSA) and incubate plate for 2 hours at 37° C.
7. Wash well thrice with PBST buffer.
8. Add secondary antibodies diluted 1:50,000 (mouse anti rabbit IgG-alkaline phosphatase conjugate in 0.01 M PBST containing 0.5% BSA) and incubate plate for 2 hours at 37° C.
9. Develop plate with Sigma Fast pNPP substrate. Stop reaction by adding 3 M NaOH and read plate absorbance at 405 nm.

The macrophage lysis assay is as follows:
1. Isolate crude extract protein from 100 mg transgenic leaf using 200 µL of extraction buffer containing CHAPS detergent (4% CHAPS, 10 mM EDTA, 100 mM NaCl, 200 mM Tris-HCl, pH 8.0, 400 mM sucrose, 14 mM β-mercaptoethanol, 2 mM PMSF) and one without CHAPS detergent.
2. Spin samples for five minutes at 10,000×g and use both supernatant and homogenate for assay
3. Plate macrophage cells RAW 264.7 (grown to 50% confluence) into 96-wells plate, incubated in 120 µL Dulbecco's Modified Eagle's Medium (DMEM; from Invitrogen life technologies).
4. Aspirate medium from wells and add 100 µL medium containing 250 ng/mL proteins in crude leaf extract.
5. In control plate, add only DMEM with no leaf fraction to test toxicity of plant material and buffers.
6. In another plate, add 40 µL dilutions onto RAW 264.7 cells from plant samples, which serially diluted 2 fold, so that the top row had plant extract at 1:14 dilution.
7. Add 20 µL of MTT 3-[4,5-dimethylthiazol-2-yl]-2,5-diphenyltetrazolium bromide; Sigma) to each well containing cells (from a stock 5 mg/ml MTT dissolved in 1×PBS and filter sterilize) after 5 hours to assess the cell death.

8. Incubate the plate at 37° C. for 5 hours. Remove media with needle and syringe. Add 200 µL of DMSO to each well and pipette up and down to dissolve crystals. Transfer to plate reader and measure absorbance at 550 nm.

Active PA was found in both the supernatant and homogenate fractions. However, maximum macrophage lysis activity was noticed in supernatant when extraction buffer was used with CHAPS detergent.

Cholera Toxin (CTB) Antigen as an Edible Vaccine.

Chloroplast transgenic plants are ideal for production of vaccines. The heatabile toxin B subunits of *E. coli* enterotoxin (LTB), or cholera toxin of *Vibrio cholerae* (CTB) have been considered as potential candidates for vaccine antigens. Integration of the unmodified native CTB gene into the chloroplast genome has demonstrated high levels of CTB accumulation in transgenic chloroplasts (Daniell, H., et al. (2001). *J. Mol. Biol.* 311, 1001-1009.). This new approach not only allowed the high level expression of native CTB gene but also enabled the multimeric proteins to be assembled properly in the chloroplast, which is essential because of the critical role of quaternary structure for the function of many vaccine antigens. The expression level of CTB in transgenic plants was between 3.5% and 4.1% tsp and the functionality of the protein was demonstrated by binding aggregates of assembled pentamers in plant extracts similar to purified bacterial antigen, and binding assays confirmed that both chloroplast-synthesized and bacterial CTB bind to the intestinal membrane GM1-ganglioside receptor, confirming correct folding and disulfide bond formation of CTB pentamers within transgenic chloroplasts (FIG. 11).

Oral Delivery of Vaccines and Selection of Transgenic Plants Without the Use of Antibiotic Selectable Markers.

Betaine aldehyde dehydrogenase (BADH) gene from spinach has been used as a selectable marker to transform the chloroplast genome of tobacco (Daniell, H. et al., (2001) *Curr. Genet.* 39, 109-116). Transgenic plants were selected on media containing betaine aldehyde (BA). Transgenic chloroplasts carrying BADH activity convert toxic BA to the beneficial glycine betaine (GB). Tobacco leaves bombarded with a construct containing both aadA and BADH genes showed very dramatic differences in the efficiency of shoot regeneration. Transformation and regeneration was 25% more efficient with BA selection, and plant propagation was more rapid on BA in comparison to spectinomycin. Chloroplast transgenic plants showed 15 to 18 fold higher BADH activity at different developmental stages than untransformed controls. Expression of high BADH level and resultant accumulation of glycine betaine did not result in any pleiotropic effects and transgenic plants were morphologically normal and set seeds as untransformed control plants.

Production of Human Therapeutic Proteins in Transgenic Chloroplasts

Human Serum Albumin (HSA) Protein.

Human Serum Albumin (HSA) accounts for 60% of the total protein in blood and widely used in a number of human therapies. Chloroplast transgenic plants were generated expressing HSA (Fernandez-San Millan et al., (2003) *Plant Bitechnol. J.* 1, 71-79). Levels of HSA expression in chloroplast transgenic plants was achieved up to 11.1% tsp. Formation of HSA inclusion bodies within transgenic chloroplasts was advantageous for purification of protein. Inclusion bodies were precipitated by centrifugation and separated easily from the majority of cellular proteins present in the soluble fraction with a single centrifugation step. Purification of inclusion bodies by centrifugation may eliminate the need for expensive affinity columns or chromatographic techniques.

Purification of HSA.

1. Solubilize the HSA inclusion bodies from transformed tissues using extraction buffer containing 0.2M NaCl, 25 mM Tris-HCl (pH 7.4), 2 mM PMSF and 0.1% Triton X-100.
2. Spin at 10,000×g. Suspend the pellet in buffer containing 6M Gu-HCl, 0.1M βME and 0.25 mM Tris-HCl (pH 7.4).
3. Dilute plant extract 100-fold in buffer containing 100 mM NaCl, 50 mM Tris-HCl (pH 8.5) and 1 mM EDTA.
4. Concentrate HSA protein by precipitation using a polyethylenglycol treatment at 37%.
5. Separate protein fractions by running a SDS-PAGE gel and stain gel with silver regent following vender's instruction (Bio-Rad, USA).

Electron Microscopy and Immunogold Labeling.

1. Cut the transformed and untransformed leaf in 1-3 mm squares.
2. Fix them in 0.1 M cacodylate buffer pH 7.4 (2.5% glutaraldehyde, 2% paraformaldehyde and 5 mM $CaCl_2$) for 15 minutes under vacuum and 12 hours at 4° C.
3. Rinse samples twice in 0.1M cacodylate buffer (pH 7.4) after fixation.
4. Dehydrate fixed samples through a graded ethanol series to 95%, then implant in LRW resin at 60° C. for 24 hours.
5. Cut ultra-thin sections using a Leica Ultracut T ultramicrotome and collect sections onto nickel grids.
6. Incubate sections in 0.05M glycine prepared in PBS buffer for 15 minutes to inactivate residual aldehyde groups.
7. Place grids onto drops of blocking solution (PBS containing 2% non-fat dry milk) and incubate for 30 minutes
8. Incubate sections for 1 hour in a goat anti-human albumin polyclonal antibody (dilution range from 1:1000 to 1:10, 000 in blocking solution).
9. Wash sections with blocking solution 6×5 minutes each.
10. Incubate sections for 2 hours with a rabbit anti-goat IgG secondary antibody conjugate to 10 nm gold diluted 1:40 in blocking solution.
11. Wash sections 6×5 minutes in blocking solution and 3×5 minutes with PBS, and fixed sections in 2% glutaraldehyde diluted in PBS for 5 minutes.
12. Wash fixed sections in PBS 3×5 minutes, then in distilled water 5×2 min each.
13. Stain sections using uranyl acetate and lead citrate and examine samples under transmission electron microscope at 60 kv.

Notes

1. Gold particles suspended in 50% glycerol may be stored for several months at −20° C. Avoid refreezing and thawing spermidine stock; use once after thawing and discard the remaining solution. Use freshly prepared $CaCl_2$ solution after filter sterilization. Do not autoclave.
2. Precipitation efficiency of DNA on gold and spreading of DNA-gold particles mixture on macrocarriers is very important. For high transformation efficiency via biolistics, a thick film of gold particles should appear on macrocarrier disks after alcohol evaporation. Scattered or poor gold precipitation reduces the transformation efficiency.
3. Generally, a 1000 bp flanking sequence region on each side of the expression cassette is adequate to facilitate stable integration of transgenes.
4. Use of the 5' untranslated region (5' UTR) and the 3' untranslated region (3' UTR) regulatory signals are necessary for higher levels of transgene expression in plastids (13). The expression of transgene in the plant chloroplast depends on a functional promoter, stable mRNA, efficient ribosomal binding sites; efficient translation is determined by the 5' and 3' untranslated regions (UTR). Chloroplast transformation elements Prrn, psbA5'UTR, 3'UTR can be amplified from tobacco chloroplast genome.

5. Bombarded leaves after two-days dark incubation should be excised in small square pieces (5-7 mm) for first round of selection and regenerated transgenic shoots should be excised into small square pieces (2-4 mm) for a second round of selection.
6. Temperature for plant growth chamber should be around 26-28° C. for appropriate growth of tobacco, potato and tomato tissue culture. Initial transgenic shoot induction in potato and tomato require diffuse light. However, higher intensity is not harmful for tobacco.
7. Transformation efficiency is very poor for both potato and tomato cultivars compared to tobacco.
8. Tobacco chloroplast vector gives low frequency of transformation if used for other plant species. For example, when petunia chloroplast flanking sequences were used to transform the tobacco chloroplast genome (DeGray, G. et al., (2001), *Plant Physiol.* 127, 852-862.), it resulted in very low transformation efficiency.

Under diffuse light conditions, highly regenerating tomato cultivar (Microtom) shoots produce premature flowering that inhibit further growth of transgenic plants. Therefore, after the first shoot induction phase, shoots should be moved to normal light conditions.

Illustrative Example 1

Transgenic chloroplast technology provides a good solution for recombinant protein production, because of the ability to achieve high expression levels, and the ability to fold and process eukaryotic proteins with disulfide bridges. To increase the expression levels, a synthetic IGF-1 (IGF-1s) gene with optimized codons for the tobacco chloroplast genome expression was made. Resulting in the AT content of 60% (increased from 41%). While expression of synthetic gene was observed in *E. coli*, no native IGF-1 gene product was detected in Western Blot. The goal was to compare expression levels of the native IGF-1 (IGF-1n) gene to the optimized, synthetic IGF-1 (IGF-1s) gene. To test the expression levels of IGF-1n and IGF-1s, tobacco plants were transformed with the chloroplast transformation vector (pLD) containing either the IGF-1s or the IGF-1n gene. The integration of the IGF-1 gene into the tobacco chloroplast genome was confirmed using PCR and Southern blot analyses. The Southern blot analysis showed that the IGF-1s and IGF-1n plants ($T_0$) were homoplasmic. The IGF-1 protein was detected in transgenic tobacco chloroplasts by western blot analysis. ELISA quantification showed that transgenic plants have an IGF-1 expression level of 12 percent of total soluble protein (% TSP) and the protein levels can be increased up to 32% TSP under continuous light. The difference in IGF-1 expression levels is very small between the synthetic and native genes inserted into the chloroplast genome. The IGF-1s plant had expression levels of 11.3% TSP and the IGF-1n plants had 9.5% TSP, suggesting that chloroplast translation machinery is quite flexible and is distinctly from *E. coli*. These results facilitate large scale production of IGF-1 at low cost. ELISA also showed exceptional stability of IGF-1 in stored leaves or crude extracts, even in the absence of protease inhibitors, facilitating long term storage after harvest.

Vector Construction:

Analysis of the codon composition of IGF-1 gene revealed a less than optimal AT content of 41%. The most highly translated protein in the chloroplast is encoded by the psbA gene; therefore codon composition of this gene served as a model for IGF-1 optimization (FIG. 1). After optimization of the IGF-1 gene, the AT content was increased from 41% to 60%. The goal of this study was to compare expression levels of the native IGF-1 (IGF-1n) gene to the optimized, synthetic IGF-1 (IGF-1s) gene. To test the expression levels of IGF-1n and IGF-1s, tobacco plants were transformed with the chloroplast transformation vector (pLD) containing either IGF-1s or IGF-1n gene. The pLD vector contains the homologous recombination sequences trnI and trnA, that allowed site specific integration into the chloroplast genome (FIG. 2a) as reported early Daniell et al (1998)[27] and Guda et al (2000)[28]. Several features account for the high protein expression levels in chloroplast transgenic plants. Both the native and synthetic genes contain the psbA 5' UTR, which enhances translation. The psbA 5' UTR is a cis acting regulatory element, controlling the translation of genes in higher plants. In addition, both constructs contain a 3' UTR, shown to increase the stability of the transcript[29]. The integration of either IGF-1 gene cassette into the inverted repeat region should double the transgene copy number.

The IGF-1 genes were fused to the ZZ tag to facilitate the purification process. Creating a fusion increases the protein's stability and protects the polypeptide from proteolytic degradation. The pLDG-IGF-1n and pLDG-IGF-1s vectors were designed with the Glu-Asn-Leu-Tyr-Phe-Gln-Gly amino acid sequence, which is recognized by the Tobacco Etch Virus (TEV) protease and cuts between the Gln-Gly (FIG. 3a). In this way, the IGF-1 polypeptide can be released without any extra amino acids.

IGF-1 Expression in *E. coli*:

According to the endosymbiotic theory, chloroplasts evolved from free-living cyanobacteria. The expression system of the chloroplast maintains many prokaryotic features. For this reason, western blot analysis was used to detect the IGF-1 expression in *E. coli*. When the two plasmids, IGF-1s and IGF-1n were tested in *E. coli*, expression of the protein was only detected in the transgenic clones with the synthetic gene (FIG. 2) and not in the native human IGF-1. Therefore this confirms that optimized gene enhances translation in a prokaryotic system (*E. coli*).

Confirmation of Integration by PCR Analysis:

Tobacco leaves were bombarded with the pLDG-IGF-1s and pLDG-IGF-1n vectors. After 48 hours of incubation in the dark, the bombarded leaves were cut and placed in RMOP medium with spectinomycin selection (500 mg/ml). This high concentration of spectinomycin helped to eliminate untransformed cells and cells in which the gene cassette integrated in the nucleus (because nuclear transformed plants do not produce enough aadA enzyme to overcome such high antibiotic selection). After four weeks the putative transgenic green shoots appeared from bleached leaves. The 3P and 3M primer pair that land in the native chloroplast genome and in the aadA gene, respectively, confirmed integration of the gene cassette into the chloroplast genome. Transformed plants that have the gene cassette integrated into the chloroplast genome showed a 1.65 kb PCR product (see FIG. 3b-c). Plants that grew in the selection media but did not show integration in the chloroplast are mutants. The PCR products were run in a 0.8% agarose gel and the shoots that show the 1.65 kb PCR product have the gene cassette integrated into the chloroplast genome. Those shoots that produced the correct size PCR product were cut into small pieces and transferred into fresh RMOP medium with spectinomycin for a second round of selection. After the shoots were obtained from the secondary selection, they were tested with the 5P-2M primers to confirm the integration of the aadA and IGF-1 genes into the tobacco chloroplast genome. The positive transgenic shoots produced a 2.5 kb PCR product (see FIG. 3d).

Figure 4A:
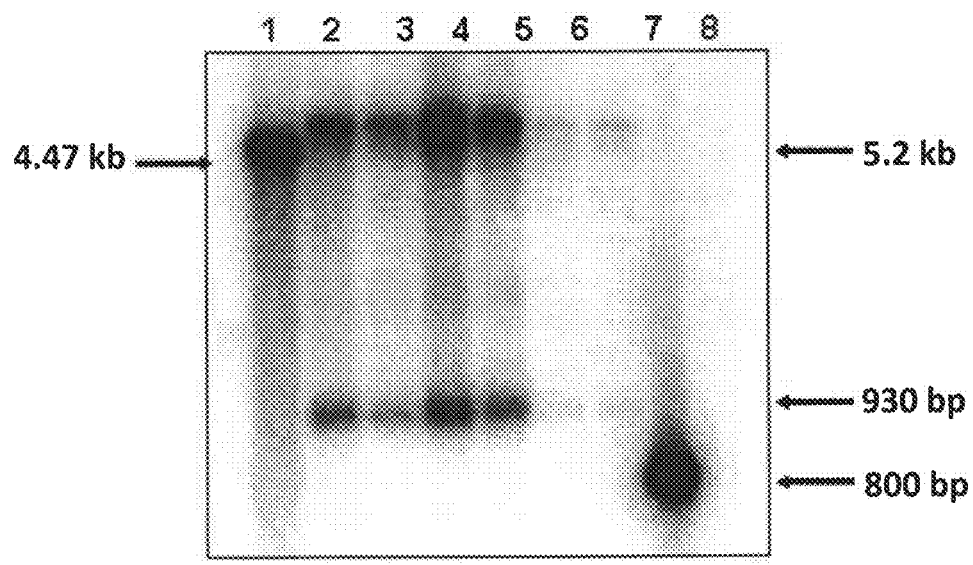
FIGS. 4A and 4B show the Southern blot analysis. The IGF-1 probe was used to confirm integration of the IGF-1 gene into the chloroplast genome.
Figure 4B:
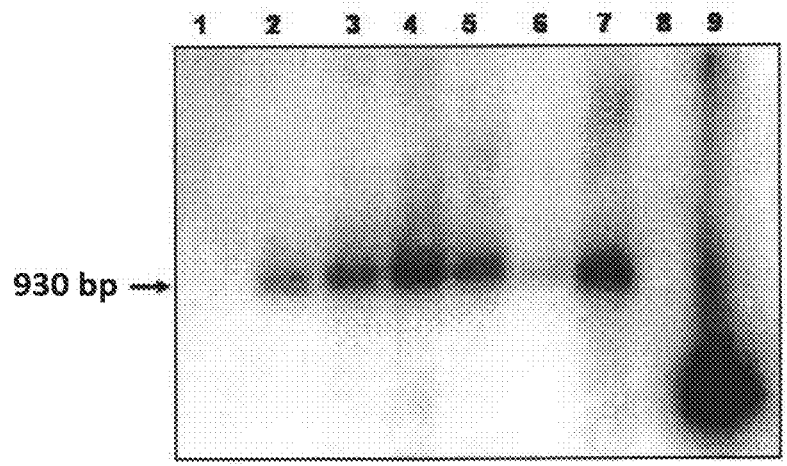

Southern Blot Analysis:

The potted plants were tested by Southern blot analysis to identify if the plants were homoplasmic or heteroplasmic. The flanking sequence probes allowed us to identify if all the chloroplast genomes are transformed (homoplasmic) or if the transformed and untransformed chloroplast genomes were present (heteroplasmic). This probe contained portion of the trnI and the trnA genes and therefore, the probe hybridized with the trnI and trnA genes that were in the chloroplast genome. The transgenic and wild type plant DNA from the plant lines were digested with Bgl II restriction endonuclease, which produced two DNA fragments (5.2 kb and 0.93 kb) in transgenic plants and one fragment of 4.47 kb in the untransformed plants. The $T_0$ transgenic plants containing the IGF-1s and the IGF-1n showed only the two fragments of the transgenic chloroplast (5.2 kb and 0.93 kb), confirming that these plants had achieved homoplasmy (FIG. 4a). The $T_1$ IGF-1s plants were also homoplasmic (the $T_1$ seeds were germinated on MSO with 500 mg/ml of spectinomycin). A second probe (IGF-1 probe) was used to confirm the integration of the IGF-1 gene into the chloroplast genome of these transgenic plants (see FIG. 4b). All of the transgenic lines showed the 930 bp fragment produced by the Bgl II digestion confirming that the IGF-1 gene was integrated into the chloroplast genome. Wild type plants did not show this fragment in the Southern blot.

Figure 5A:
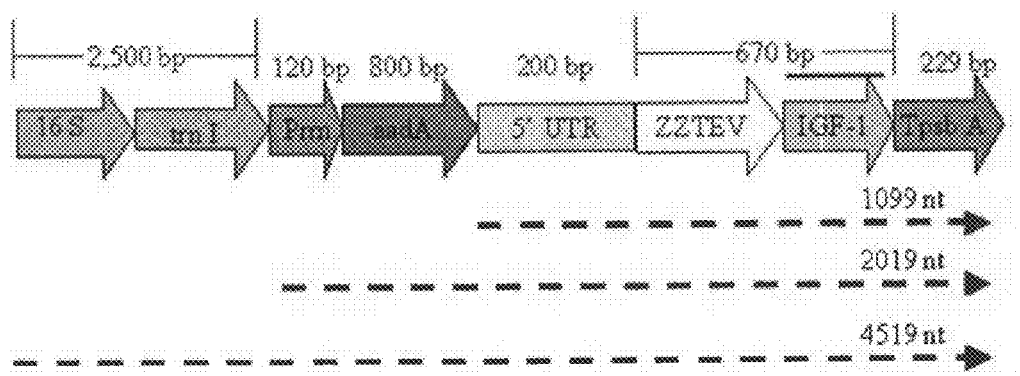
FIGS. 5A and 5B show the Northern blot analysis.
Figure 5B:
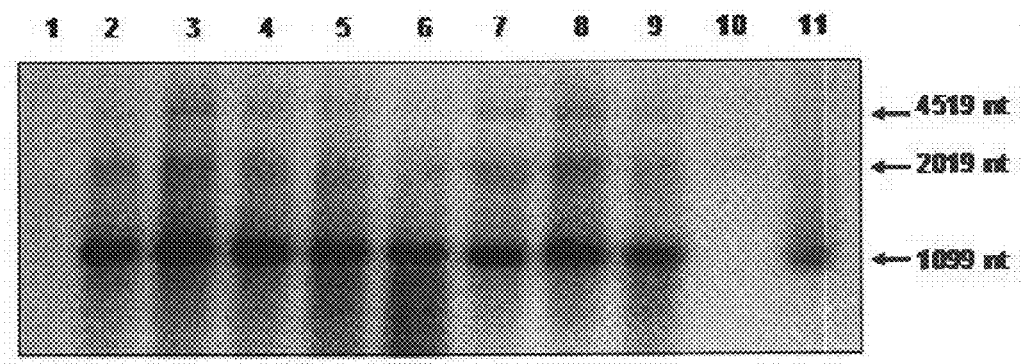

Northern Blot Analysis:

The potted plants were grown in a photoperiod of 16 hours of light and 8 hours of dark at 27° C. RNA was extracted from transformed and untransformed tobacco plant to use for the northern blot analysis. Transcripts of about 1099 nucleotides were observed in the transgenic plants, which contains the psbA promoter, 5' UTR, the IGF-1 gene, and psbA 3' UTR. This mRNA is considered monocistronic and it is the most abundant transcript in all transgenic plants (see FIG. 5). In addition, dicistronic and polycistronic transcripts were found in lower abundance in the chloroplast transgenic plants. Northern blot analysis also showed that the IGF-1s and the IGF-1n plants had equally high rates of transcription and there were no significant differences at the transcriptional level between the IGF-1n and IGF-1s plants. Also, unusual transcripts were not observed in the native gene, confirming lack of non-specific processing of transcripts.

Figure 6:
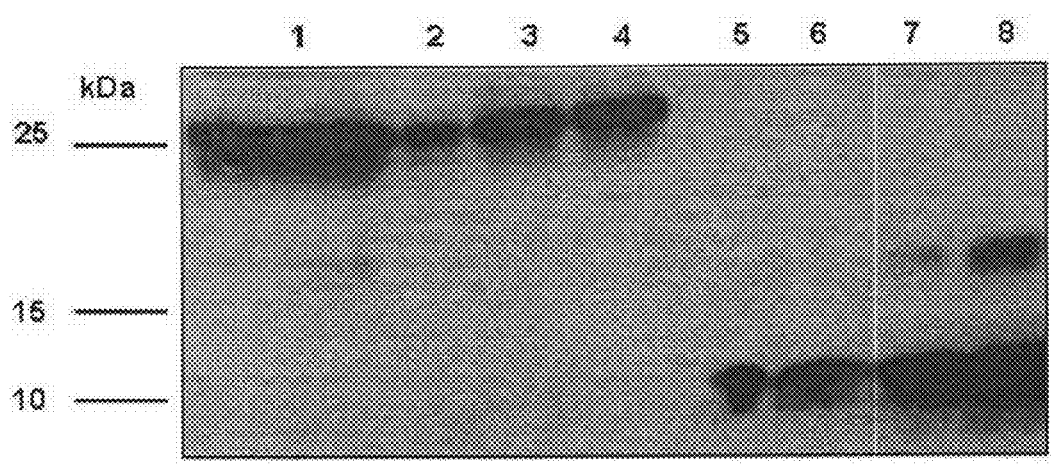
FIG. 6 shows the plant Western Blot Analysis. The plant samples were run in 12% SDS-PAGE and the blot was detected using mouse anti-human IGF-1. Lane 1 shows a plant transformed with 5'UTR-ZZTEV-IGF-1n. Lanes 2 and 5 are blank. Lane 3 is T0 plant transformed with 5'UTR-ZZTEV-IGF-1s. Lane 4 shows the T1 transformed with 5'UTR-ZZTEV-IGF-1s. Lanes 6 to 8 show standards with a concentration of 10 ng, 25 ng, and 50 ng.
Figure 7A:
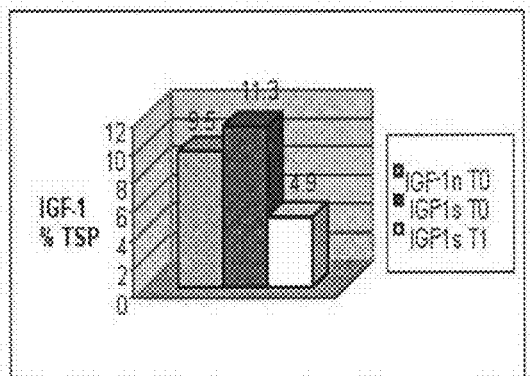
FIGS. 7A-7F show the IGF-1 expression in transgenic chloroplasts. The ELISA shows IGF-1 expression as percentage of total soluble protein.
Figure 7B:
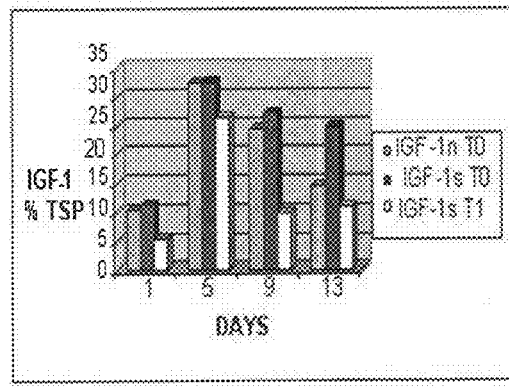

IGF-1 Expression in Transgenic Chloroplast:

The Western blot was made using protein extracts from plants that were growing in a photoperiod of 16 hours of light and 8 hours of dark. The blot showed that the plants transformed with IGF-1s and IGF-1n genes were expressing the IGF-1 polypeptide, which had a molecular weight of 24 kDa (see FIG. 6). The Gel-Doc was used to quantify the amount of IGF-1 expressed in the different transgenic lines. The IGF-1n-plant had an expression level of 10.9 IGF-1 percentage of total soluble proteins (% TSP). The IGF-1s-plant ($T_0$) had a 12.5 IGF-1% TSP and the T1 plant (T1 plant is a younger plant and T0 is a mature plant) had a 4.8 IGF-1% TSP. An ELISA was performed on the same plants to have more accurate protein quantification. The ELISA showed that IGF-1n plant had an expression level of 9.5 IGF-1% TSP. The IGF-1s-plant (T0) had 11.3 IGF-1% TSP and the T1 plant had 4.9 IGF % TSP (see FIG. 7a). Thus, expression levels were confirms by both method. This also indicates that IGF-1 polypeptide is in the soluble fraction.

Figure 7C:
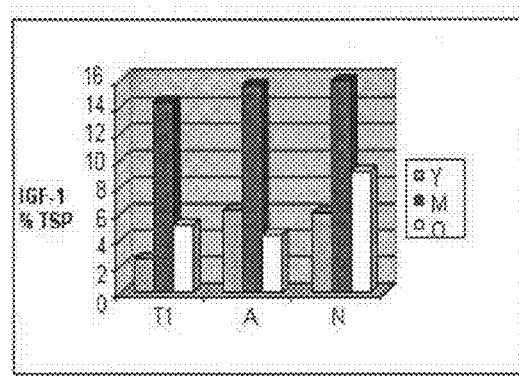
Figure 7D:
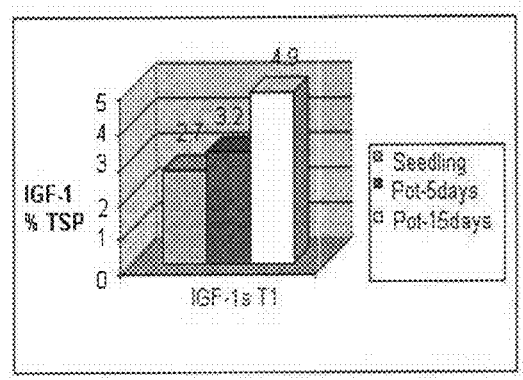
Figure 7E:
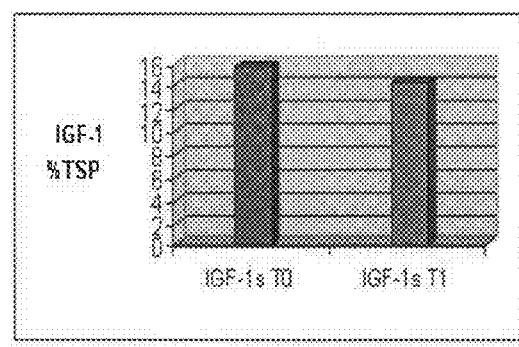
Figure 7F:
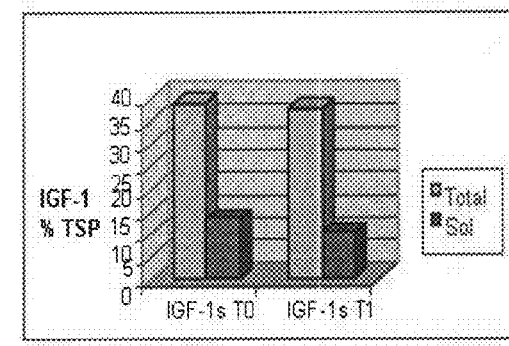
Figure 8:
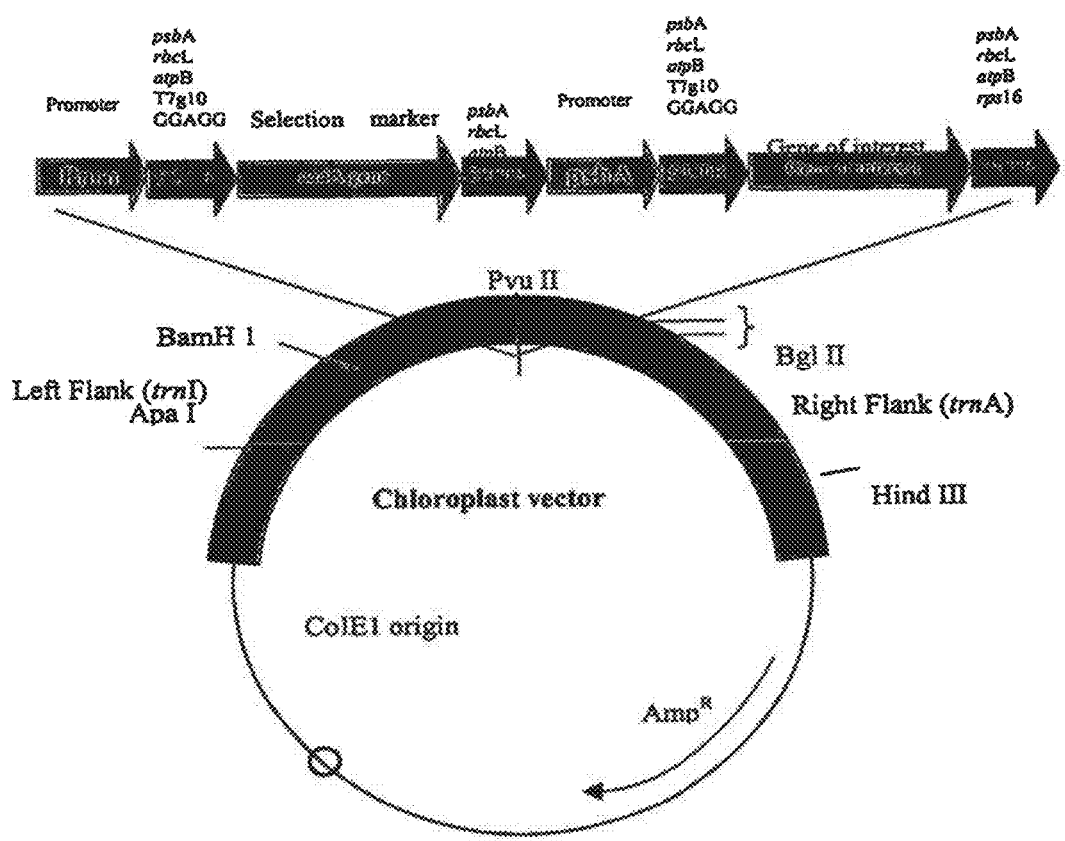
FIG. 8 shows a schematic view of a general plastid transformation vector.

The transgenic plants were exposed to continuous light for 5 days to enhance the IGF-1 expression levels, because the psbA 5' UTR is light regulated. ELISAs showed more than 2 fold increase in the expression levels after the plants were incubated for 5 days in continuous light. The IGF-1s-plant ($T_0$) had an IGF-1 expression levels of 32.7% TSP and $T_1$ plant had 26.6% TSP. The IGF-1n-plant ($T_0$) had an expression levels of 32.4% TSP. The expression levels were measured again alter 9 and 13 days. For both IGF-1s and IGF-1n, the ELISAs showed a decrease in the expression levels (FIG. 6b). A third experiments were done to quantify the IGF-1 expression during plant development. The IGF-1s seeds were germinated in MSO media with 500 ng/ml of spectinomycin. A seedling with 5 days in the pot and 15 days in the pot were used for this assay. The seedling had an expression level of 2.7 IGF-1% TSP, the 5 days in pot plant was expressing 3.2 IGF-1% TSP and the 15 days in pot plant had an IGF-1 amount of 4.9 IGF-1% TSP (see FIG. 7d). Additionally, IGF-1 protein accumulation was measured in young, mature, and scenescing leaves. A young leaf was taken from the top five leaves, the mature leaf was green and fully-grown from the mid-section of the plant, and the old leaf was scenescent and from the very bottom of the plant. FIG. 7c shows that all transgenic lines had a higher IGF-1 expression in mature leaves and the amount of IGF-1 decreased in scenesing leaves. The ELISA showed that the expression levels between the $T_0$ and the $T_1$ in the plant that contain the IGF-1s were very similar, the $T_0$ had % TSP and the $T_1$ had % TSP (FIG. 7e). The amount of IGF-1 was measure in the total plant extract and the soluble fraction this assay showed that the total plant extracts had a % TSP and the soluble fraction had % TSP.

DISCUSSION

Transgenic chloroplast plants are expressing large amounts of human IGF-1. The difference in IGF-1 expression levels is insignificant between the synthetic and native genes in the chloroplasts. The IGF-1 expression level in the IGF-1s $T_0$ plant is 11.3 IGF-1% TSP (FIG. 7) and in the IGF-1n $T_0$ plant is 9.5 IGF-1% TSP. On the contrary, the IGF-1 polypeptide was only expressed in the E. coli cells that contain the IGF-1s. These results show the first time that E. coli translational machinery may be different from chloroplast.

The psbA 5'UTR was used in the pLDG-IGF-1n and pLDG-IGF-1s vectors to enhance the protein expression. The psbA 5'UTR is light regulated. The transgenic plants were grown in continuous light for two weeks. The expression levels increased more than 2 fold (see FIG. 7b) after five days in continuous light, then the IGF-1 expression levels decreased after 9 and 13 days. A possible explanation is that the tobacco plants were producing a protease, which was degrading the IGF-1 polypeptide because the plants were under the biological stress of continuous light. Then protein expression was measured in young, mature and old leaves. The IGF-1 expression was higher in mature leaves (see FIG. 7), but the amount of IGF-1 decreased in the scenscing leaves, due to increased in proteolytic activity. These results support the idea that the IGF-1 polypeptide had been degraded by proteases in scenescent leaves. Stored of powdered leaf for long periods should facilitate long term storage of leaves before extraction of IGF-1.

In summary, genetic engineering of the chloroplast genome is an ideal expression system because the high copy number dramatically increases the foreign protein expression levels. This research demonstrates that IGF-1 can be expressed in high amounts in tobacco plants. Investigations are in progress to test if the transgenic plants are producing the mature IGF-1 and that the protein is fully functional.

MATERIALS AND METHODS

Recursive PCR and Primer Design:

For synthesis of optimized IGF-1 (IGF-1s) gene, four primers were designed: two external primers of 56 bp and two internal of 100 bp. All the primers have an overlapping region of 20 bp. The 5'external primer was engineered to include the sequence of the TEV enzymatic cleave site and the 3'primer contained the NotI restriction site. In recursive PCR reaction, the external oligonucleotides were in higher concentration than the internal (20-30 pmol of the external primers and 0.2-0.3 pmol of the internal primers). The lower concentration of the internals oligonucleotides assisted in avoiding unwanted products.

Two different parts were use in the recursive PCR. In the first part, the reaction were run through 10 cycles using the following temperature sequence: 94° C. for 30 seconds to denature the DNA, 55° C. for 30 seconds for annealing primes, and 72° C. for 1 minute to synthesize DNA. An incubation period of 7 minutes at 72° C. followed after the cycles ended. The primers were designed to have an annealing temperature of 55° C. to avoid unspecific binding of the primers. The second part consisted of 30 cycles, denaturing the DNA for 30 seconds at 94° C., then primers annealing for 30 seconds at 65° C., followed by a DNA synthesis for 7 minutes at 72° C. The PCR product was run on 1.5% agarose gel at 65 volts for 55 minutes to visualize amplified products. The IGF-1s was cloned into the pBluescript KS II, and E. coli cells were transformed with this vector.

Bombardment and Selection of Transgenic Plants:

Sterile leaves were bombarded using the Bio-Rad PDS-1000/He biolistic device. The bombarded leaves were incubated in the dark for 48 hours and then cut and placed in RMOP medium with 500 µg/ml of spectinomycin.

PCR Analysis:

The plant DNA was extracted from the leaves using the Qiagen Dneasy Plant Mini Kit (Quiagen). The 3P and 3M primers were used to perform a PCR on transformed and untransformed plants[27-28]. Samples were run for 30 cycle with the following sequence: 94° C. for 1 min., 65° C. for 1.5 min., and 72° C. for 2 min. PCR products were run on 0.8% agarose gel.

Southern Blot Analysis:

The plant DNA of the transgenic and wild type tobacco plants were digested with BglII, and separated on 0.8% agarose gel and transferred to a nylon membrane. The 0.8 kb probe was generated by digesting pLD-CtV2 (that contain portion of the trnI and trnA genes) vector with BamHI and BglII and was labeled with $^{32}P$ (Amersham). The probe was hybridized with the membrane using the QUICK-HYB hybridization solution and protocol (Stratagen).

Western Blot Analysis:

One hundred mg of transgenic tobacco leaves as well as untransformed were ground in liquid nitrogen and resuspended in 200 µl of extraction buffer (200 mM Tris-HCl, pH 8.0, 100 mM NaCl, 10 mM EDTA, 4 mM PMSF) (Arakawa et al., 1997). Then leaf extracts were boiled for 5 minutes in the sample buffer (0.5M Tris-HCl, pH 6.8, 2.5 ml glycerol, 10% SDS, 0.5% bromophenol blue reached a total volume 9.5 ml with water) (Bio-Rad). All samples were electrophoresed in 15% resolving and 4% stacking gels using the buffer system of Laemmli. The membrane was blocked for 20 minutes at room temperature with PBS and 3% non-fat milk (PBS-milk). Then, the blot was incubated with anti-IGF-1 (Upstate Biotechnology) (diluted in PBS-milk until it achieved a final concentration 1 µg per ml) overnight at 4° C. The membrane was wash twice with water. The secondary antibody used was a Goat Anti Mouse IgG conjugated to Horseradish Peroxidase (American Qualex Antibodies) at a 1:5000 dilution, and was added to the membranes in blocking solution and incubated for one hour. The blot was washed with water. A final wash was done for 5 minutes in PBS with 0.05% Tween 20. Development was performed by the chemiuluminecent method (Pierce).

ELISA:

ELISA was used to quantify the IGF-1 expression levels in different transgenic lines. Different concentrations of 100 mg leaves (transformed and untransformed plants) were ground with liquid nitrogen. Five hundred µl of bicarbonate buffer, pH 9.6 (15 mM $Na_2CO_3$, 35 mM $NaHCO_3$, and 0.1% Tween 20, pH 9.6) was used to resuspend the ground mixture and incubated overnight at 4° C. The samples were diluted (1:3000), 1 µl of the plant extraction and 3 ml of bicarbonate buffer. 100 µl of the sample was added in each well of the plate and this was done in duplicate. Only bicarbonate buffer was added to one well of the plate. This well was considered the blank. The plate was incubated overnight at 4° C. After washing the wells thrice with washing buffer, PBST (PBS and 0.05% Tween 20), mouse anti human IGF-1 diluted 1 µg/ml in 0.01 M PBST containing 0.3% milk (100 µl/well) was added and incubated for 2 h at 37° C. The wells were washed and incubated with 1:10,000 goat anti mouse IgG-alkaline phosphatase conjugate in 0.01 M PBST containing 0.3% milk (100 µl/well) for 2 h at 37° C. The plate was developed with TMB substrate (100 µl/well) (American Qualex) for 30 minutes at room temperature and the reaction was ended by addition of 50 µl/well of 2M sulfuric acid and the plates were read at 405 nm. For a standard curve, purified commercially available human IGF-1 (R&D Systems) was diluted with bicarbonate buffer to concentrations between 3 and 25 ng/ml and processed as above.

Total soluble plant protein concentration was determined using the DC Protein Microassay (Bio-Rad). IGF-1 expression levels were calculated as a percentage of total soluble protein.

All references cited to herein and all references listed in the reference section of this Application are incorporated by reference.

REFERENCES

1. Spencer, E., Skover, G., and Hunt T. (1988) Growth Factors and Other Aspects of Wound Healing: Biological and Clinical Implication. Alan R. Liss, New York, pp. 103-116.
2. Feld, S., Hirschberg, R. (1996) Growth Hormone, the Insulin-like Growth Factor System, and the Kidney. Endocr. Rev. 17:423-80.
3. Walsh, G. (1998) Biopharmaceuticals: Biochemistry and Biotechnology. Jhon Wiley and sons. First edition, England. 235-243.
4. Kim, S. and Lee, Y. (1996) High-level Expression and Simple Purification of Recombinand Human Insulin-like Growth Factor I. J. of Biotechnology. 48:97-105.
5. Blomsma, M., Knegt, R., Dullaart, R., and Jansen, P. (1997) Insulin-like Growth Factor-I in Liver Cirrhosis. J. Hepatology. 27:1133-38.
6. Picardi, A., Costa de Oliveira, A., Muguerza, B., Tosar, A., Quiroga, J., Castilla-Cortázar, I., Santidrián, S., and Prieto, J. (1997) Low doses of insulin-like growth factor-I improve nitrogen retention and food efficiency in rats with early cirrhosis. J. Hepatology 26: 191-202.
7. Castilla-Cortázar, L, Prieto, J., Urdaneta, E., Pascual, M., Nuñez, M., Zudaire, E., García, M., Quiroga, J., and Santidrian, S. (1997). Impaired Intestinal Sugar Transport in Cirrhotic Rats: Correction by low doses of Insulin-like Growth Factor I. Gastroenterology 113: 1180-1187.
8. Castilla-Cortázar, I., Picardi, A., Tosar, A., Ainzúa, J., Urdaneta, E., Garcia, M., Pascual, M., Quiroga, J., and Prieto, J. (1999). Effect of insulin-like growth factor I on in vivo intestinal absorption of D-galactose in cirrhotic rats. American Journal Physiology 276 (39): G37-G42.
9. Castilla-Cortazar, I., García, M., Quiroga, J., Diez, N., Diez-Caballero, F., Calvo, A., Diaz, M., and Prieto, J. (2000). Insulin-like Growth Factor-I Reverts Testicular Atrophy in Rats With Advanced Cirrhosis. Hepatology 31: 592-600.
10. Castilla-Cortázar, I., García, M., Muguerza, B., Quiroga, J., Perez, R., Santidrian, S., and Prieto, J. (1997). Hepatoprotective effects of Insulin-like Growth Factor I in Rats with Carbon Tetrachloride-induced Cirrhosis. Gastroenterology 113: 1682-1691.
11. Laron, Z., Anin, S., Klipper-Aurbach, Y., and Klinger, B. (1992). Effects of insulin-like growth factor on linear growth, head circumference, and body hair in patients with Laron-type dwarfism. Lancet 339: 1258-1261.
12. Bach, M., Chin. E., and Bondy, C. (1993). The effects of recombinant insulin-like growth factor I (IGF-I) on growth hormone, IGF-II, IGF binding protein and blood glucose levels in normal and diabetic adolescents. Ped. Res 33:190-198.
13. Bondy, C. (1994). Clinical uses of insulin-like growth factor I. Ann. Intern. Med 120:593-601.
14. Ebeling, P., Jones, J., O'Fallon, W., Janes, C., and Riggs, B. (1993). Short-term effects of recombinant human insulin growth factor I on bone turnover in normal women. J. Clin. Endocrinol. Metab. 77: 1384-1387.
15. Kozakowski, J., Papierska, L., Krassowski, J., and Zgliczynski, S. (1998). The effect of growth hormone replacement therapy on markers of bone formation and bone mineral density in elderly men. Pol. Arch. Med. Wewn. 100: 306-312.
16. Fleming, R., Rutan, R., Jahoor, F., Barrow, R., Wolfe, R., and Herndon, D. (1992). Effect of recombinant human insulin-like growth hormone on catabolic hormones and free fatty acids following thermal injury. J. Traumatol. 32: 698-703.
17. Lieberman, S., Butterfield, G., Harrison, D., and Hoffman, A. (1994). Anabolic effects of recombinant insulin-like growth factor I in cachetic patients with the acquired immunodeficiency syndrome. J. Clin. Endocrinol. Metab. 78: 404-410.
18. Moks, T., Abrahamsen, L., Osterlof, B., Josephson, S., Ostling, M. (1987). Large scale affinity purification of human insulin like growth factor I from culture medium of E. coli. Biotechnology 5: 379-382.
19. Kusnadi, A., Nikolov, Z., Howard, J. (1997). Production of Recombinant proteins in Transgenic plants: Practical considerations. Biotechnology and Bioengineering. 56 (5): 473-484.
20. Giddings, G., Allison, G., Brooks, D., and Carter A. (2000) Transgenic Plant as Factories for Biopharmaceuticals. Nat. Biotechnology. 18(11):1151-5.
21. Sijmons, P., Dekker, B., Schrammeijer, B., Verwoerd, T., van den Elzen, P., and Hoekema. A. (1990) Production od Correctly processed Human Serum Albumin in Transgenic Plant. Biotechnology. 8(3):217-21.
22. Dieryck, W., Pagnier, J., Poyart, C., Marden, M., Gruber, V., Bournat, P., Baudino, S., and Merot, B. (1997) Human Hemoglobin from Transgenic Tobacco. Nature. 6; 386: 29-30.
23. May, G., Mason, H., Lyons, P. (1996). Application of transgenic plants as production systems for pharmaceuticals in ACS symposium series 647. Fuller et al eds., chapter 13, 196-204.
24. Daniell, H., Khan, M., and Allison, L. (2002) Milestone in Chloroplast Genetic Engineering: an environmentally friendly era in biotechnology. Trends in Plant Science. 7(2): 84-91.
25. De Cosa, B., Moar, W., Lee, S., Miller, M., and Daniell, H. (2000) Overexpression of the Bt cry 2Aa2 Operon in Chloroplasts Leads to Formation of Insecticidal Crystals. Nature Biotechnology. 19:71-74.
26. Daniell, H., Lee, S., Panchal, T., Wiebe, P. (2001) Expression of Cholera Toxin B Subunit Gene and Assembly as Functional Oligomers in Transgenic Chloroplasts. J. Mol. Biol. 311(5):1001-09.
27. Daniell, H. Datta, R., Gray, S., Varme, S., and Lee, S. (1998) Containment of Herbicide Resistance Through Genetic Engineering of the Chloroplast Genome. Nat. Biotechnol. 16:345-58.
28. Guda, C., Lee, S., and Daniell, H. (2000) Stable Expression of a Biodegradable Protein-based Polymer in Tobacco Chloroplasts. Plant Cell Rep. 19:257-62.
29. Eibl, C., Zou, Z., Kim, M., Mullet, J., and Koop, H. (1999) In vivo Analysis of Plastid psbA, rbcL, and rpl32 UTR Elements by Chloroplast Transformation: Tobacco Plastid Gene Expression is Controlled by Modulation of Transcript Levels and Translation Efficiency. Plant J. 19:333-45.
30. Prodromou, C. and Pearl, L. (1992) Recursive PCR: a novel technique for total gene synthesis. Protein Engineering. 5(8):827-29.
31. Casimiro, D., Wright, P., and Dyson, H. (1997) PCR-based gene synthesis and protein NMR spectroscopy. Structure. 5:1407-12.
32. Daniell, H. (1993) Foreign Gene Expression in Chloroplasts of Higer Plant mediated by Tungsten Particle Bombardment. Methods Enzymol. 217:536-56.
33. Daniell, H. (1997) Transformation and Foreign Gene Expression in Plants Mediated by Microprojectile Bombardment. Methods Mol. Biol. 62:463-89.

What is claimed is:

1. A vector for transforming a plastid genome, said vector comprising, as operably-linked sequences, a trnI flanking sequence, a promoter operative in a plastid genome operably linked to a 5' untranslated region (UTR) sequence, a DNA sequence comprising SEQ ID NO:2, which encodes insulin-like growth factor-1 (IGF-1), a 3' untranslated region (UTR) sequence, and a trnA flanking sequence, wherein said vector comprises an expression cassette encoding an antibiotic-free selectable marker also located between the flanking sequences.

2. The vector of claim 1, wherein said 5' and 3' UTRs comprise psbA 5' and psbA 3' sequence elements.

3. A vector for transforming a plastid genome, said vector comprising, as operably-linked sequences, a trnI flanking sequence, a promoter operative in a plastid genome operably linked to a 5' untranslated region (UTR) sequence, a DNA sequence comprising SEQ ID NO:2, which encodes insulin-like growth factor-1 (IGF-1) for expression in said plastid genome, a 3' untranslated region (UTR) sequence, and a trnA flanking sequence, wherein said vector comprises an expression cassette encoding Betaine aldehyde dehydrogenase (BADH) also located between the flanking sequences.

4. A method for producing IGF-1, said method comprising: integrating the vector of claim 1 into a plastid genome of a plant cell; and growing said plant cell to thereby express the IGF 1.

5. A recombinant plant, progeny or seed transformed with the transformation vector of claim 1.

6. The plant of claim 5, wherein said plant is an edible plant suitable for mammal consumption.

7. A plant containing at least one chloroplast transformed with the vector of claim 1.

8. A recombinant plant, progeny or seed transformed with the transformation vector of claim 3.

9. The plant of claim 8, wherein said plant is an edible plant suitable for mammal consumption.

* * * * *

SEQUENCE LISTING

```
<160> NUMBER OF SEQ ID NOS: 3

<210> SEQ ID NO 1
<211> LENGTH: 210
<212> TYPE: DNA
<213> ORGANISM: Homo sapiens

<400> SEQUENCE: 1
ggaccggaga cgctctgcgg ggctgagctg gtggatgctc ttcagttcgt gtgtggagac      60
```

```
agggcttttt atttcaacaa gcccacaggg tatggctcca gcagtcggag ggcgcctcag      120
acaggcatcg tggatgagtg ctgcttccgg agctgtgatc taaggaggct ggagatgtat      180
tgcgcacccc tcaagcctgc caagtcagct                                        210

<210> SEQ ID NO 2
<211> LENGTH: 210
<212> TYPE: DNA
<213> ORGANISM: Artificial Sequence
<220> FEATURE:
<223> OTHER INFORMATION: Synthetic IGF-1

<400> SEQUENCE: 2
ggtcctgaaa ctttatgtgg tgctgaatta gtagatgctt tacaattcgt atgtggtgat       60
cgtggtttct atttcaacaa acctactggt tacggttctt cttctcgtcg tgctcctcaa      120
actggtattg tagatgaatg ttgtttccgt tcttgtgatt tacgtcgttt agaaatgtac      180
tgtgctcctt taaaacctgc taaatctgct                                        210

<210> SEQ ID NO 3
<211> LENGTH: 7
<212> TYPE: PRT
<213> ORGANISM: Artificial Sequence
<220> FEATURE:
<223> OTHER INFORMATION: Tobacco Etch Virus protease site

<400> SEQUENCE: 3

Glu Asn Leu Tyr Phe Gln Gly
1               5
```